United States Patent
Liras

(10) Patent No.: US 6,720,336 B2
(45) Date of Patent: Apr. 13, 2004

(54) 4,4-BIARYLPIPERIDINE DERIVATIVES

(75) Inventor: Spiros Liras, Stonington, CT (US)

(73) Assignees: Pfizer, Inc., New York, NY (US);
Pfizer Products, Inc., Groton, CT (US)

( * ) Notice: Subject to any disclaimer, the term of this patent is extended or adjusted under 35 U.S.C. 154(b) by 0 days.

(21) Appl. No.: 09/901,825

(22) Filed: Jul. 10, 2001

(65) Prior Publication Data

US 2002/0013321 A1 Jan. 31, 2002

Related U.S. Application Data

(63) Continuation of application No. 09/323,332, filed on Jun. 1, 1999, now abandoned.
(60) Provisional application No. 60/099,565, filed on Sep. 9, 1998.

(51) Int. Cl.[7] ................. A61K 31/445; C07D 211/22; C07D 211/32
(52) U.S. Cl. ............. 514/317; 514/326; 546/208; 546/211; 546/212; 546/214; 546/236
(58) Field of Search .................. 514/317, 326; 546/208, 211, 212, 214, 236

(56) References Cited

U.S. PATENT DOCUMENTS

| 4,016,280 A |   | 4/1977 | Menge et al. ............. 514/317 |
| 5,994,369 A | * | 11/1999 | Kolassa et al. ............. 514/317 |

FOREIGN PATENT DOCUMENTS

| DE | 1936452 | * | 2/1971 |
| DE | 2139084 |   | 8/1971 |
| DE | 2139085 | * | 2/1973 |
| DE | 2166997 |   | 12/1977 |
| EP | 0657428 |   | 6/1995 |
| WO | WO 94/26712 |   | 11/1994 |
| WO | WO 96/31208 |   | 10/1996 |
| WO | WO 97/42956 |   | 11/1997 |
| WO | 97/42956 | * | 11/1997 |
| WO | WO 97/45423 |   | 12/1997 |
| WO | 97/45423 | * | 12/1997 |

OTHER PUBLICATIONS

Huegi et al. "Synthesis and analgesic properties . . . " CA 102:220708 (1984).*
O'Brien "Recptor binding in drug research" Marcel Dekker, p. 185–187 (1987).*
Pan "Mu–opposing actions of the kappa opioid receptor" Trends in Pharm v. 19 p. 94–98 (1998).*
copies provied in parent case.*
Huegi et al., Synthesis and Analgesic Properties . . . ; Chemical Abstracts 102:220708 (1984).
O'Brien, Receptor binding in drug research; Marcel Dekker, p. 185–87, 192 (1987).
Pan, Mu–opposing actions of the kappa opiod receptor: Trends in Pharm. V. 19, p. 94–98 (1998).
Dieter Neuser, et al., European Journal of Pharmacology, 87, (1983), pp. 315–318.
Chemical Abstracts, vol. 98, no. 21, May 23, 1983 Abstract # 172575f.

* cited by examiner

*Primary Examiner*—Ceila Chang
(74) *Attorney, Agent, or Firm*—Scully, Scott, Murphy & Presser

(57) ABSTRACT

The present invention relates to compounds of the formula I,

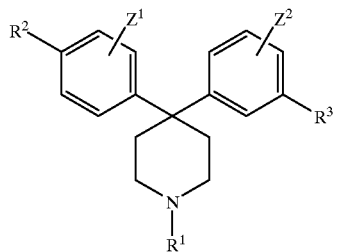

wherein $Z^1$, $Z^2$, $R^1$, $R^2$ and $R^3$ are defined as in the specification, pharmaceutical compositions containing such compounds the use of such compounds to treat neurological and gastrointestinal disorders.

11 Claims, No Drawings

4,4-BIARYLPIPERIDINE DERIVATIVES

The present application is a continuation of U.S. application Ser. No. 09/323,332 filed Jun. 1, 1999, now abandoned which claims priority under 35 USC section 119 of U.S. provisional application No. 60/099,565 filed Sep. 9, 1998. The complete text of the 09/323,332 application is incorporated by reference herein, as if fully set forth.

BACKGROUND OF THE INVENTION

This invention relates to 4,4-biarypiperidine derivatives which have utility as ligands for opioid receptors.

In the study of opioid biochemistry, a variety of endogenous opioid compounds and non-endogenous opioid compounds has been identified. In this effort, significant research has been focused on understanding the mechanism of opioid drug action, particularly as it relates to cellular and differentiated tissue opioid receptors.

Opioid drugs are typically classified by their binding selectivity in respect of the cellular and differentiated tissue receptors to which a specific drug species binds as a ligand. These receptors include mu ($\mu$), delta ($\delta$) and kappa ($\kappa$) receptors.

At least three subtypes of opioid receptors (mu, delta and kappa) are described and documented in the scientific literature. All three receptors are present in the central and peripheral nervous systems of many species including man. Activation of delta receptors produces antinociception in rodents and can induce analgesia in man, in addition to influencing motility of the gastrointestinal tract. (See Burks, T. F. (1995) in "The Pharmacology of Opioid Peptides", edited by Tseng, L. F., Harwood Academic Publishers).

The well known narcotic opiates such as morphine and its analogs are selective for the opioid mu receptor. Mu receptors mediate analgesia, respiratory depression, and inhibition of gastrointestinal transit. Kappa receptors mediate analgesia and sedation.

The existence of the opioid delta receptor is a relatively recent discovery which followed the isolation and characterization of endogenous enkephalin peptides, which are ligands for the delta receptor. Research in the past decade has produced significant information about the delta receptor, but a clear picture of its function has not yet emerged. Delta receptors mediate analgesia, but do not appear to inhibit intestinal transit in the manner characteristic of mu receptors.

U.S. Pat. No. 4,816,586, which issued on Mar. 28, 1989 to P. S. Portoghese, refers to various delta opioid receptor antagonists. These compounds are described as possessing a unique opioid receptor antagonist profile, and include compounds that are highly selective for the delta opioid receptor.

U.S. Pat. No. 4,518,711, which issued May 21, 1985 to V. J. Hruby et al., describes cyclic, conformationally constrained analogs of enkephalins. These compounds include both agonists and antagonists for the delta receptor, and are said to induce pharmacological and therapeutic effects, such as analgesia in the case of agonist species of such compounds. The antagonist species of the disclosed compounds are suggested to be useful in the treatment of schizophrenia, Alzheimer's disease, and respiratory and cardiovascular functions.

S. Goenechea, et al, in "Investigation of the Biotransformation of Meclozine in the Human Body," *J. Clin. Chem. Clin. Biochem.,* 1988, 26(2), 105–15, describe the oral administration of a polyaryl piperazine compound in a study of meclozine metabolization in human subjects.

In "Plasma Levels, Biotransformation and Excretion of Oxatomide in Rats, Dogs, and Man," *Xenobiotica,* 1984, 15(6), 445–62, Meuldermans, W., et al. refer to a metabolic study of plasma levels, biotransformation, and excretion of oxatomide.

T. Iwamoto, et al, in "Effects of KB-2796, A New Calcium Antagonist, and Other Diphenylpiperazines on [$^3$H] nitrendipine Binding", *Jpn. J. Pharmacol.,* 1988, 48(2), 241–7, describe the effect of a polyaryl piperazine as a calcium antagonist.

K. Natsuka, et al, in "Synthesis and Structure-Activity Relationships of 1-Substituted 4-(1,2-Diphenylethyl) piperazine Derivatives Having Narcotic Agonist and Antagonist Activity," *J. Med. Chem.,* 1987, 30 (10), 1779–1787, disclose racemates and enantiomers of 1-substituted 4-[2-(3-hydroxyphenyl)-1-phenylethyl] piperazine derivatives.

European Patent Application No. 458,160, published on Nov. 27, 1991, refers to certain substituted diphenylmethane derivatives as analgesic and antiinflammatory agents, including compounds wherein the methylene bridging group (linking the two phenyl moieties) is substituted on the methylene carbon with a piperidinyl or piperazinyl group.

South African Patent Application No. 8604522, which was published on Dec. 12, 1986, refers to certain N-substituted arylalkyl and aryl-alkylene substituted aminoheterocyclic compounds, including piperdine derivatives, as cardiovascular, antihistamine, and anti-secretory agents.

European Patent Application No. 133,323, published on Feb. 20, 1985, refers to certain diphenylmethyl piperazine compounds as non-sedative antihistamines.

There is a continuing need in the art for improved opioid compounds, particularly compounds which are free of addictive character and other adverse side effects of conventional opiates such as morphine and pethidine.

The present inventor has discovered a novel class of 4,4-biarylpiperidine derivatives that are potent and selective delta opioid ligands and are useful for treatment of rejection in organ transplants and skin grafts, epilepsy, chronic pain, neurogenic pain, nonsomatic pain, stroke, cerebral ischemica, shock, head trauma, spinal cord trauma, brain edema, Hodgkin's disease, Sjogren's disease, systemic lupus erythematosis, gastrointestinal disorders such as gastritis, functional bowel disease, irritable bowel syndrome, functional diarrhoea, functional distention, non-ulcerogenic dyspepsia and other disorders of motility or secretion, and emesis, acute pain, chronic pain, neurogenic pain, nonsomatic pain, allergies, respiratory disorders such as asthma, cough and apnea, inflammatory disorders such as rheumatoid arthritis, osteoarthristis, psoriasis and inflammatory bowel disease, urogenital tract disorders such as urinary incontinence, hypoxia (e.g., perinatal hypoxia), hypoglycemic neuronal damage, chemical dependencies and addictions (e.g., a dependency on, or addiction to opiates, benzodiazepines, cocaine, nicotine or ethanol), drug or alcohol withdrawal symptoms, and cerebral deficits subsequent to cardiac bypass surgery and grafting.

SUMMARY OF THE INVENTION

This invention relates to compounds of the formula

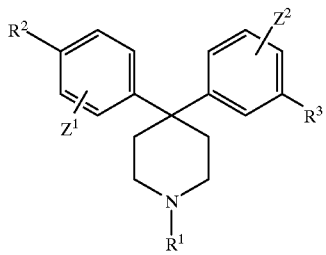

wherein $R^1$ is hydrogen, $(C_0-C_8)$alkoxy-$(C_0-C_8)$alkyl-, wherein the total number of carbon atoms is eight or less, aryl, aryl-$(C_1-C_8)$alkyl-, heteroaryl, heteroaryl-$(C_1-C_8)$alkyl-, heterocyclic, heterocyclic-$(C_1-C_8)$alkyl, $(C_3-C_7)$cycloalkyl-, or $(C_3-C_7)$cycloalkyl-$(C_1-C_8)$alkyl, wherein said aryl and the aryl moiety of said aryl-$(C_1-C_8)$alkyl- are selected, independently, from phenyl and napthyl, and wherein said heteroaryl and the heteroaryl moiety of said heteroaryl-$(C_1-C_8)$ alkyl- are selected, independently, from pyrazinyl, benzofuranyl, quinolyl, isoquinolyl, benzothienyl, isobenzofuryl, pyrazolyl, indolyl, isoindolyl, benzimidazolyl, purinyl, carbazolyl, 1,2,5-thiadiazolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, oxazolyl, oxadiazolyl, isoxazoyl, thiazolyl, isothiazolyl, furanyl, pyrazolyl, pyrrolyl, tetrazolyl, triazolyl, thienyl, imidazolyl, pyridinyl, benzooxazolyl and pyrimidinyl; and wherein said heterocyclic and the heterocyclic moiety of said heterocyclic-$(C_1-C_8)$alkyl- are selected from saturated or unsaturated nonaromatic monocyclic or bicyclic ring systems, wherein said monocyclic ring systems contain from four to seven ring carbon atoms, from one to three of which may optionally be replaced with O, N or S, and wherein said bicyclic ring systems contain from seven to twelve ring carbon atoms, from one to four of which may optionally be replaced with O, N or S; and wherein any of the aryl, heteroaryl or heterocyclic moieties of $R^1$ may optionally be substituted with from one to three substitutuents, preferably with one or two substutituents, independently selected from halo (i.e., chloro, fluoro, bromo or iodo), $(C_1-C_6)$ alkyl optionally substituted with from one to seven (preferably with from zero to four) fluorine atoms, phenyl, benzyl, hydroxy, acetyl, amino, cyano, nitro, $(C_1-C_6)$alkoxy, $(C_1-C_6)$alkylamino and $[(C_1-C_6)$alkyl$]_2$amino, and wherein any of alkyl moieties in $R^1$ (e.g., the alkyl moieties of alkyl, alkoxy or alkylamino groups) may optionally be substituted with from one to seven (preferably with from zero to four) fluorine atoms;

$R^2$ is hydrogen, aryl, heteroaryl, heterocyclic, $SO_2R^4$, $COR^4$, $CONR^5R^6$, $COOR^4$, or $C(OH)R^5R^6$ wherein each of $R^4$, $R^5$ and $R^6$ is defined, independently, as $R^1$ is defined above, or $R^5$ and $R^6$, together with the carbon or nitrogen to which they are both attached, form a three to seven membered saturated ring containing from zero to three heterocarbons selected, independently, from O, N and S, and wherein said aryl, heteroaryl, and heterocyclic are defined as such terms are defined above in the definition of $R^1$, and wherein any of the aryl, heteroaryl and heterocyclic moieties of $R^2$ may optionally be substituted with from one to three substitutuents, preferably with one or two substutituents, independently selected from halo (i.e., chloro, fluoro, bromo or iodo), $(C_1-C_6)$alkyl optionally substituted with from one to seven (preferably with from zero to four) fluorine atoms, phenyl, benzyl, hydroxy, acetyl, amino, cyano, nitro, $(C_1-C_6)$alkoxy optionally substituted with from one to seven (preferably with from zero to four) fluorine atoms, $(C_1-C_6)$alkylamino and $[(C_1-C_6)$alkyl$]_2$amino;

$R^3$ is hydroxy, $(C_1-C_6)$ alkoxy, $NHSO_2R^7$, $C(OH)R^7R^8$, fluorine or $CONHR^7$, wherein $R^7$ and $R^8$ are the same or different and are selected from hydrogen, $(C_1-C_4)$ alkyl, $(C_1-C_4)$alkoxy and $(C_1-C_4)$alkoxy-$(C_1-C_4)$alkyl having a total of 4 or less carbon atoms, and wherein any of the alkyl moieties of $R^7$ and $R^8$ may optionally be substituted with from one to seven (preferably with from zero to four) fluorine atoms; and $Z^1$ and $Z^2$ are selected, independently, from hydrogen, halo and $(C_1-C_5)$alkyl;

with the proviso that there are no two adjacent ring oxygen atoms and no ring oxygen atom adjacent to either a ring nitrogen atom or a ring sulfur atom in any of the heterocyclic or heteroaryl moieties of formula I;

and the pharmaceutically acceptable salts of such compounds.

Preferred compounds of the formula I include those wherein $R^1$ is cyclopropylmethyl, 3-cyclohexylpropyl, 2-phenylethyl, 2-methylpentyl, p-methylbenzyl, 2,2,2-trifluoroethyl, or 1-methylpentyl.

Other examples of preferred compounds of the formula I are those wherein $R^2$ is diethyl amide, methyl ethyl amide, a diethyl carbinol, tetrazole, or pyrazole.

Other examples of preferred compounds of the formula I are those wherein $R^3$ is hydroxy, fluoro, $CONH_2$, $NHSO_2CH_3$, or methoxy.

The compounds of formula I and their pharmaceutically acceptable salts are opioid receptor ligands and are useful in the treatment of a variety of neurological and gastrointestinal disorders. Examples of disorders that can be treated with the compounds of formula I and their pharmaceutically acceptable salts are rejection in organ transplants and skin grafts, epilepsy, chronic pain, neurogenic pain, nonsomatic pain, stroke, cerebral ischemica, shock, head trauma, spinal cord trauma, brain edema, Hodgkin's disease, Sjogren's disease, systemic lupus erythematosis, gastrointestinal disorders such as gastritis, functional bowel disease, irritable bowel syndrome, functional diarrhoea, functional distention, nonulcerogenic dyspepsia and other disorders of motility or secretion, and emesis, acute pain, chronic pain, neurogenic pain, nonsomatic pain, allergies, respiratory disorders such as asthma, cough and apnea, inflammatory disorders such as rheumatoid arthritis, osteoarthritis, psoriasis and inflammatory bowel disease, urogenital tract disorders such as urinary incontinence, hypoxia (e.g., perinatal hypoxia), hypoglycemic neuronal damage, chemical dependencies and addictions (e.g., a dependency on, or addiction to opiates, benzodiazepines, cocaine, nicotine or ethanol), drug or alcohol withdrawal symptoms, and cerebral deficits subsequent to cardiac bypass surgery and grafting.

The present invention also relates to the pharmaceutically acceptable acid addition and base addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts. The chemical bases that are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium, calcium and magnesium, etc.

The present invention also relates to the pharmaceutically acceptable base addition salts of compounds of the formula I. These salts are all prepared by conventional techniques. The chemical bases that are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium, calcium and magnesium, etc.

For a review on pharmaceutically acceptable salts, see Berge et al., J. Pharm. Sci., 66, 1–19 (1977).

This invention also relates to a pharmaceutical composition for treating a disorder or condition, the treatment or prevention of which can be effected or facilitated by modulating (i.e., increasing or decreasing) binding to opioid receptors in a mammal, including a human, comprising an amount of a compound of the formula I, or a pharmaceutically effective salt thereof, that is effective in treating such disorder or condition and a pharmaceutically acceptable carrier.

This invention also relates to a method of treating a disorder or condition, the treatment of which can be effected or facilitated by modulating binding to opioid receptors in a mammal, comprising administering to a mammal in need of such treatment an amount of a compound of the formula I, or a pharmaceutically effective salt thereof, that is effective in treating such disorder or condition.

This invention also relates to a pharmaceutical composition for treating a disorder or condition selected from inflammatory diseases such as arthritis (e.g., rheumatoid arthritis and osteoarthritis), psoriasis, asthma, or inflammatory bowel disease, disorders of respiratory function such as asthma, cough and apnea, allergies, gastrointestinal disorders such as gastritis, functional bowel disease, irritable bowel syndrome, functional diarrhoea, functional distension, functional pain, nonulcerogenic dyspepsia and other disorders of motility or secretion, and emesis, stroke, shock, brain edema, head trauma, spinal cord trauma, cerebral ischemia, cerebral deficits subsequent to cardiac bypass surgery and grafting, urogential tract disorders such as urinary incontinence, chemical dependencies and addictions (e.g., addictions to or dependencies on alcohol, opiates, benzodiazepines, nicotine, heroin or cocaine), chronic pain, nonsomatic pain, acute pain and neurogenic pain, systemic lupus erythematosis, Hodgkin's disease, Sjogren's disease, epilepsy and rejection in organ transplants and skin grafts in a mammal, including a human, comprising a glutamate neurotransmission modulating effective amount of a compound of the formula I, or a pharmaceutically salt thereof, and a pharmaceutically acceptable carrier.

This invention also relates to a method for treating a condition selected from inflammatory diseases such as arthritis, psoriasis, asthma, or inflammatory bowel disease, disorders of respiratory function such as asthma, cough and apnea, allergies, gastrointestinal disorders such as gastritis, functional bowel disease, irritable bowel syndrome, functional diarrhoea, functional distension, functional pain, nonulcerogenic dyspepsia and other disorders of motility or secretion, and emesis, stroke, shock, brain edema, head trauma, spinal cord trauma, cerebral ischemia, cerebral deficits subsequent to cardiac bypass surgery and grafting, urogential tract disorders such as urinary incontinence, chemical dependencies and addictions (e.g., addictions to or dependencies on alcohol, opiates, benzodiazepines, nicotine, heroin or cocaine), chronic pain, nonsomatic pain, acute pain and neurogenic pain, systemic lupus erythematosis, Hodgkin's disease, Sjogren's disease, epilepsy and rejection in organ transplants and skin grafts, in a mammal, comprising administering to such mammal, including a human, an opioid receptor binding modulating effective amount of a compound of the formula I, or a pharmaceutically acceptable salt thereof.

This invention also relates to a pharmaceutical composition for treating a disorder or condition, the treatment of which can be effected or facilitated by modulating binding to opioid receptors in a mammal, including a human, comprising an opioid receptor binding modulating effective amount of a compound of the formula I, or a pharmaceutically acceptable salt thereof, and a pharmaceutically acceptable carrier.

This invention also relates to a method for treating a disorder or condition, the treatment of which can be effected or facilitated by modulating in a mammal, including a human, comprising administering to such mammal an opioid receptor binding modulating effective amount of a compound of the formula I or a pharmaceutically acceptable salt thereof.

This invention also relates to a method of treating a condition selected from inflammatory diseases such as arthritis, psoriasis, asthma, or inflammatory bowel disease, disorders of respiratory function such as asthma, cough and apnea, allergies, gastrointestinal disorders such as gastritis, functional bowel disease, irritable bowel syndrome, functional diarrhoea, functional distension, functional pain, nonulcerogenic dyspepsia and other disorders of motility or secretion, and emesis, stroke, shock, brain edema, head trauma, spinal cord trauma, cerebral ischemia, cerebral deficits subsequent to cardiac bypass surgery and grafting, urogential tract disorders such as urinary incontinence, chemical dependencies and addictions (e.g., addictions to or dependencies on alcohol, opiates, benzodiazepines, nicotine, heroin or cocaine), chronic pain, nonsomatic pain, acute pain and neurogenic pain, systemic lupus erythematosis, Hodgkin's disease, Sjogren's disease, epilepsy and rejection in organ transplants and skin grafts in a mammal, comprising administering to a mammal in need of such treatment an amount of a compound of the formula I that is effective in treating such condition.

This invention also relates to a pharmaceutical composition for treating a condition selected from inflammatory diseases such as arthritis, psoriasis, asthma, or inflammatory bowel disease, disorders of respiratory function such as asthma, cough and apnea, allergies, gastrointestinal disorders such as gastritis, functional bowel disease, irritable bowel syndrome, functional diarrhoea, functional distension, functional pain, nonulcerogenic dyspepsia and other disorders of motility or secretion, and emesis, stroke, shock, brain edema, head trauma, spinal cord trauma, cerebral ischemia, cerebral deficits subsequent to cardiac bypass surgery and grafting, urogential tract disorders such as urinary incontinence, chemical dependencies and addictions (e.g., addictions to or dependencies on alcohol, opiates, benzodiazepines, nicotine, heroin or cocaine), chronic pain, nonsomatic pain, acute pain and neurogenic pain, systemic lupus erythematosis, Hodgkin's disease, Sjogren's disease, epilepsy and rejection in organ transplants and skin grafts in a mammal, comprising an amount of a compound of the formula I that is effective in treating such condition and a pharmaceutically acceptable carrier.

Unless otherwise indicated, the alkyl groups referred to herein, as well as the alkyl moieties of other groups referred to herein (e.g., alkoxy), may be linear or branched, and they may also be cyclic (e.g., cyclopropyl, cyclobutyl, cyclopentyl, or cyclohexyl) or be linear or branched and contain cyclic moieties.

The term "alkoxy", as used herein, means "—O-alkyl", wherein "alkyl" is defined as above.

The term "alkylene", as used herein, means an alkyl group having two available binding sites (i.e., -alkyl-, wherein alkyl is defined as above).

The term "treating" as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

Unless otherwise indicated, "halo" and "halogen", as used herein, refer to fluorine, bromine, chlorine or iodine.

Compounds of the formula I may have chiral centers and therefore may exist in different enantiomeric and diastereomic forms. This invention relates to all optical isomers and all other stereoisomers of compounds of the formula I, and to all racemic and other mixtures thereof, and to all pharmaceutical compositions and methods of treatment defined above that contain or employ such isomers or mixtures.

Formula I above includes compounds identical to those depicted but for the fact that one or more hydrogen or carbon atoms are replaced by isotopes thereof. Such compounds are useful as research and diagnostic tools in metabolism pharmokinetic studies and in binding assays. Specific applications in research include radioligand binding assays, autoradiography studies and in vivo binding studies.

DETAILED DESCRIPTION OF THE INVENTION

The compounds of formula I can be prepared according to the methods illustrated in Schemes 1–9 and discussed below. In the reaction schemes and discussion that follow, unless otherwise indicated, $Z^1$, $Z^2$, $R^1$, $R^2$, and $R^3$ and structural formula I are defined as above.

Scheme 1 illustrates a method for the preparation of compounds with the general formula I wherein $R^3$ is $(C_1–C_6)$alkoxy or fluorine, $R^2$ is $CONR^5R^6$ and $R^1$ is as defined above with the proviso that it is not attached to the piperidine nitrogen at a secondary alkyl carbon or an aryl group. Referring to Scheme 1, a bromobenzene derivative of formula 0, wherein $R^3$ is methoxy or fluorine, is cooled to −70° C. in dry tetrahydrofuran, and then a solution of n-butyllithium is added to it. The resulting solution is then treated with N-benzylpiperidinone and the solution is allowed to warm to room temperature to produce the corresponding compound of formula 1.

Alternatively, the benzene derivative of formula 0 in tetrahydrofuran can be treated with magnesium at a temperature from about 0° C. to the reflux temperature, preferably starting at room temperature for about three hours and then heating to reflux and letting the reaction proceed for another hour, after which N-benzylpiperidinone is added to the mixture. The resulting solution is then stirred at a temperature ranging from about 0° C. to the reflux temperature, preferably at about room temperature, to produce the corresponding compound of formula 1.

The compound of formula 1, produced by either of the above methods, in dichloroethane is then treated with phenol and aluminum chloride or another Lewis acid (e.g., boron trifluoride etherate), and the resulting solution is stirred at a temperature ranging from about 0° C. to the reflux temperature, preferably at about the reflux temperature, to produce the corresponding phenol derivative of formula 2. The compound of formula 2 is then treated with trifluoromethane sulfonic anhydride or another suitable reagent such as N-phenyltrifluoromethanesulfonimide, in the presence of a base such as pyridine, triethylamine, another trialkyl amine, an alkali metal hydride or an alkali metal carbonate, to form the trifluoromethane sulfonate ester of formula 3. This reaction is typically performed in dicloromethane at a temperature ranging from about 0° C. to the reflux temperature, preferably at about room temperature.

The compound of formula 3 is placed under a carbon monoxide atmosphere at a pressure ranging from about 14 to 100 psi, in a solution of dimethylsulfoxide and a lower alkanol such as methanol or ethanol, with a suitable trialkylamine base (e.g., triethylamine) and palladium acetate with 1,3-bis(diphenylphosphino)propane (DPPP) or another suitable palladium ligand. Other suitable palladium catalysts such as bis(triphenylphosphine) palladium dichloride may also be used. This reaction is performed at temperatures ranging from about 20° C. to 100° C.

Treatment of the ester of formula 4 with an aluminum amide of a primary or secondary amine, for example, diethyl amine, in a solvent such as dichloroethane or toluene, at a temperature ranging from about 20° C. to about the reflux temperature, preferably at about the reflux temperature, yields the corresponding amide of formula 5. Variations in the nature of the $R^1$ group on the piperidine nitrogen can be effected in the following manner, as illustrated by process steps (5→6→7) in Scheme 1. The compound of formula 5 is placed under a hydrogen atmosphere at pressures ranging from about 14 to 100 psi, in ethanol or other another solvent such as acetic acid or methanol, to produce the corresponding compound of formula 6. This reaction is typically carried out at a temperature from about 0° C. to about the reflux temperature, preferably at about room temperature.

Treatment of the compound of formula 6 with an aldehyde and sodium triacetoxyborohydride or another reducing agent (e.g., sodium borohydride or sodium cyanoborohydride), in dichloromethane, 1,2 dichloroethane or another suitable solvent such as methanol, ethanol or toluene, at a temperature ranging from about 0° C. to 100° C., preferably at about room temperature, yields the desired compound of formula 7.

SCHEME 1

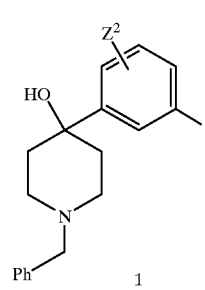

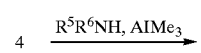

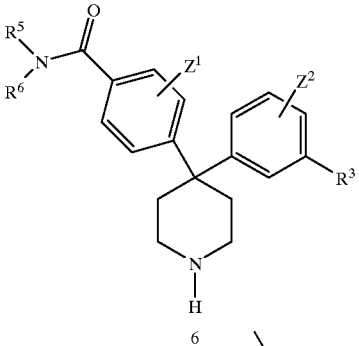

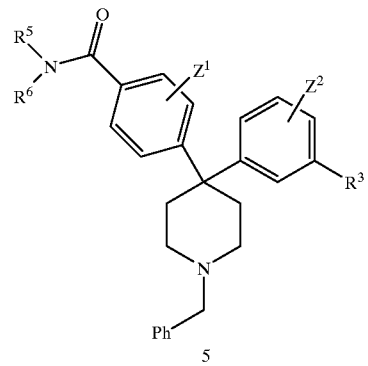

Compounds of formula I wherein $R^1$ is a group that attaches to the piperidine nitrogen via an aryl moiety or a primary or secondary alkyl moiety, can be prepared by treating the corresponding compound of formula 6 with an alkylating or arylating agent of the formula $R^1X$, wherein X is a leaving group such as chloro, bromo, iodo, triflate (OTf), mesylate (OMs) or tosylate (Ots), and sodium or potassium carbonate or another alkali metal carbonate or bicarbonate in a solvent such as dimethylformamide, dichloromethane or 1,2 dichloroethane, at a temperature ranging from about 20° C. to 100° C., as shown below in Scheme 2.

In connection with the definition of formula $R^1X$ in the case where X is an aldehyde moiety (CHO), it is noted that the aldehyde carbon attaches to the piperidine nitrogen and thus $R^1$ would include an additional carbon atom, which fact is reflected in Example 16 (reactant F→reactant G) where the designation $R^XCHO$ was used.

reflux temperature is preferred when hydrobromic acid/acetic acid is used, and about 100° C. to about 120° C. is preferred when sodium ethanemethiolate is used.

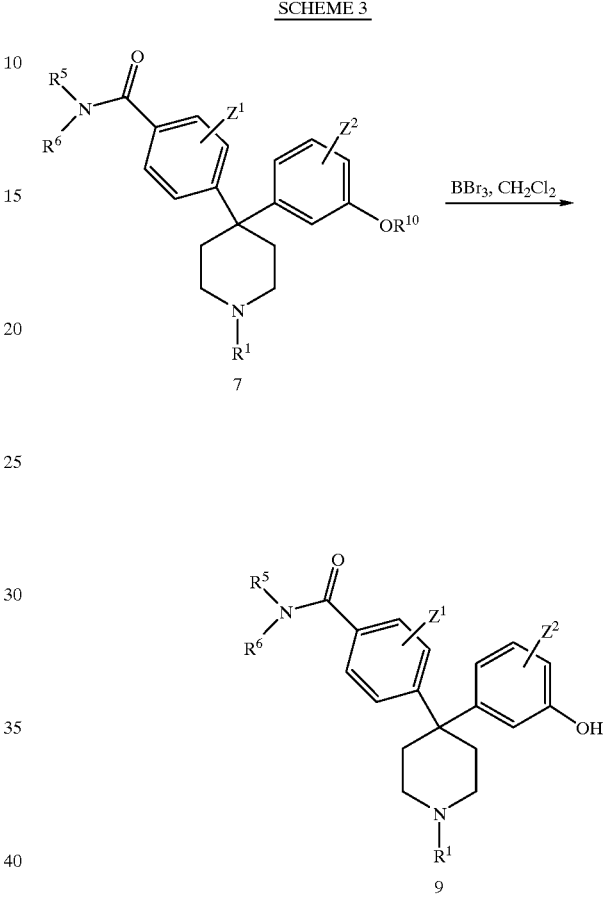

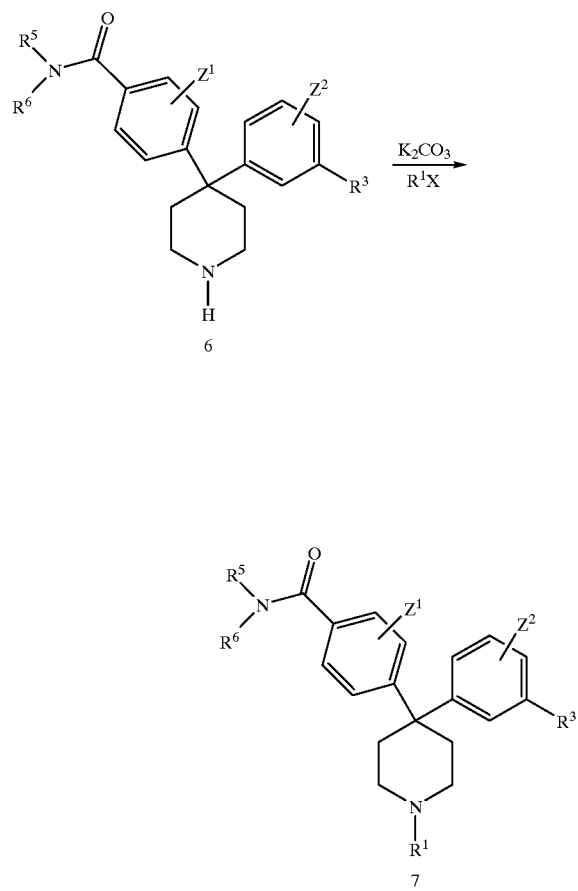

Compounds of the general formula I where $R^3$ is hydroxy can be prepared by deprotecting the corresponding alkyl ether of formula 7 (wherein $R^{10}$ is $(C_1-C_6)$alkyl) with boron tribromide in dicloromethane, or with aqueous hydrobromic acid and acetic acid, or with sodium ethanethiolate in dimethyiformamide, at a temperature ranging from about 0° C. to the reflux temperature, as shown in Scheme 3. Room temperature is preferred when boron tribromide is used, the Compounds of the general formula I where $R^3$=CONHR can be prepared from the corresponding phenols of formula 9 as illustrated in Scheme 4 below. This can be accomplished by formation of the triflate of formula 10 using conditions identical to those used for the preparation of compounds of the formula 3 (Scheme 1). The compound of formula 10 is then converted to the corresponding ester of formula 11 using conditions identical to those used in the preparation of esters of the formula 4 (Scheme 1). Treatment of the compound of formula 11 with an aluminum amide of an amine in a solvent such as toluene or 1,2 dichloroethane, at a temperature ranging from about 0° C. to about the reflux temperature, preferably at about the reflux temperature, or treatment of the same with a lithium amide in ether or tetrahydrofuran at a temperature ranging from about −78° C. to the reflux temperature, preferably at about −78° C., yields the desired compound of formula I wherein $R^3$=CONHR$^4$ and $R^4$ is (formula 12 below).

SCHEME 4

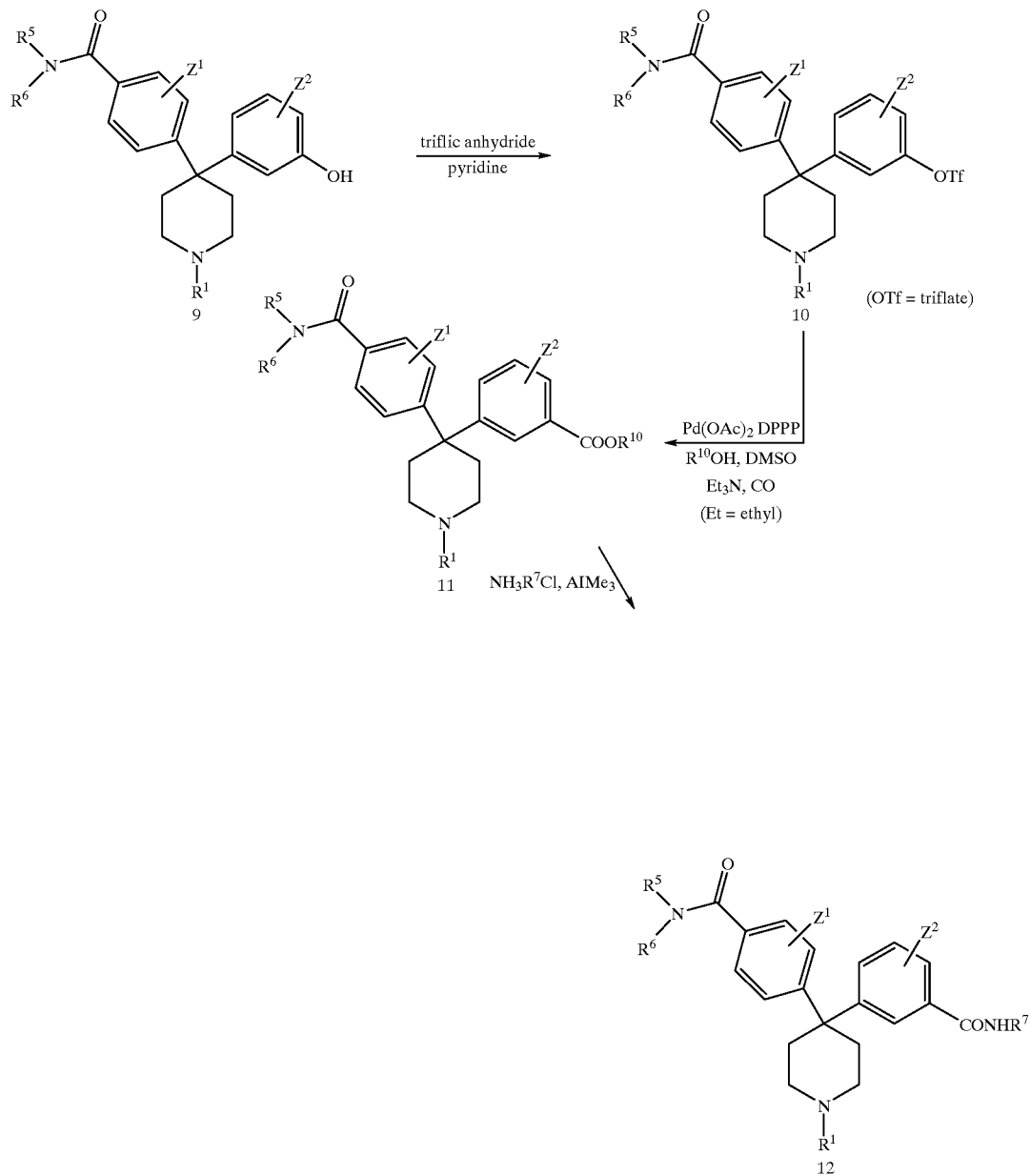

Alternatively, the carboxamide of formula 12 can be accessed by conversion of the triflate ester of formula 10 into the nitrile of formula 13 by treatment with zinc cyanide and a palladium catalyst such as tetrakis triphenylphosphine palladium, in a solvent such as dimethylformamide, or toluene, at a temperature from about 0° C. to about the reflux temperature, preferably at about the reflux temperature. The nitrile of formula 13 can be converted into the carboxamide of formula 12 by treatment with hydrogen peroxide and sodium carbonate in ethanol, at a temperature ranging from about 0° C. to about the reflux temperature, preferably at about room temperature.

SCHEME 4A

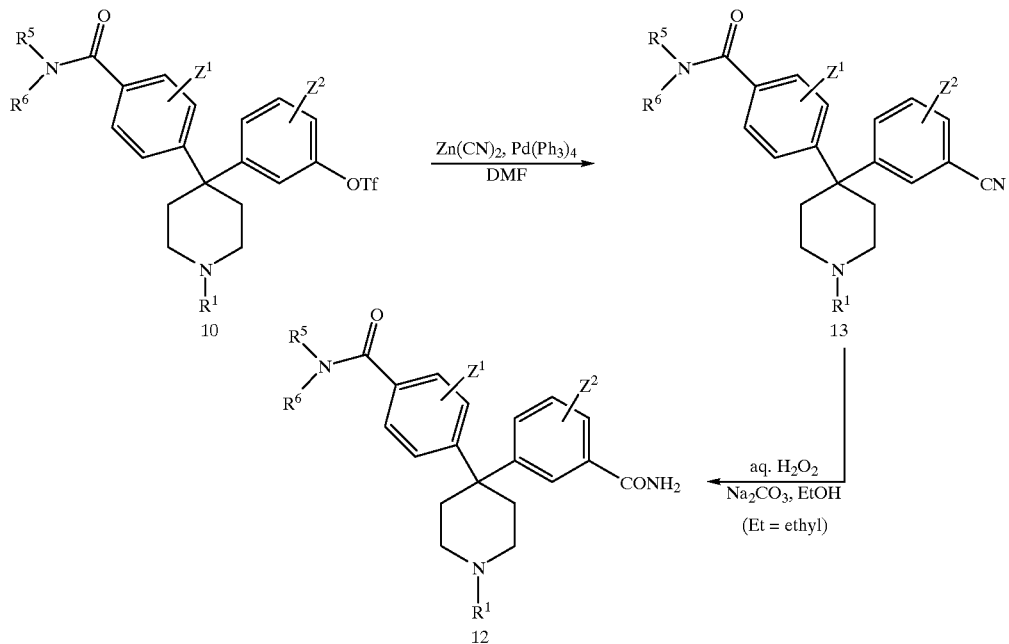

Compounds of the general formula I where $R^3$ is $NHSO_2R^5$ can be prepared, as illustrated in Scheme 5, by hydrolysis of the ester of formula 11 to the carboxylic acid of formula 14 by reacting it with lithium hydroxide or another alkali metal hydroxide in a mixture of tetrahydrofuran (THF) and water, at a temperature from about room temperature to about the reflux temperature. The compound of formula 14 is then converted into the aniline of formula 15 by reaction with diphenylphosphoryl azide in the presence of triethylamine or another trialkylamine base, in t-butanol at the reflux temperature, followed by acid hydrolysis with aqueous hydrochloric acid in ethyl acetate or with trifluoroacetic acid in methylene chloride. The compound of the formula 15 is then sulfonylated to produce the desired compound of formula 16 with an aryl- or alkylsulfonyl chloride and pyridine triethylamine or another trialkylamine base in dichloromethane, dichloroethane or toluene, at temperatures from about 0° C. to about the reflux temperature, preferably at about room temperature.

SCHEME 5

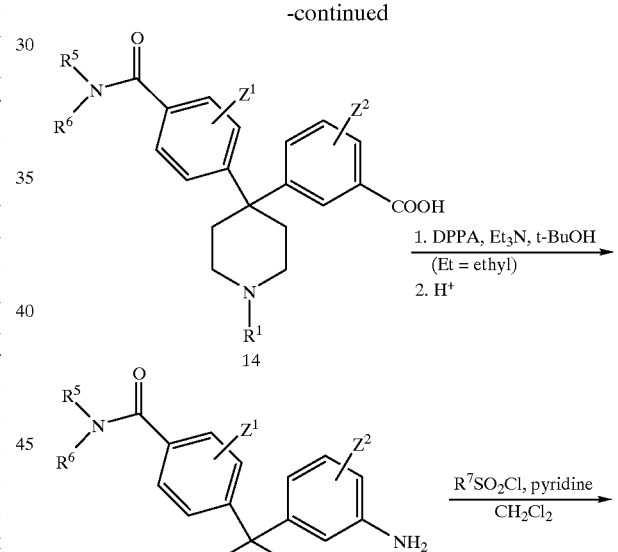

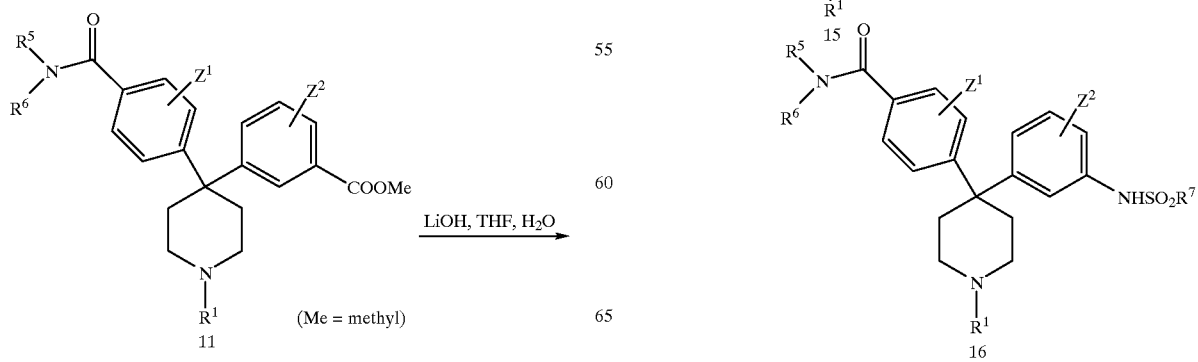

Compounds of the general formula I wherein $R^3$ is methoxy, hydroxy or fluorine and $R^2$ is an aromatic or heteroaromatic moiety (referred to in Scheme 6 as compounds of the formula 17) can be prepared by organometalic coupling of a compound of the formula 3 with an aryl and heteroaryl boronic acid, wherein aryl and heteroaryl are defined as in the definitions of $R^1$ and $R^2$, in a solvent such as ethanol or toluene, in the presence of a of palladium catalyst such as tetrakis triphenylphosphine palladium and a trialkylamine base (e.g., triethylamine) or alkali metal carbonate base, as shown below in Scheme 6. This reaction is generally carried out at a temperature from about room temperature to about the reflux temperature, preferably at about the reflux temperature.

SCHEME 6

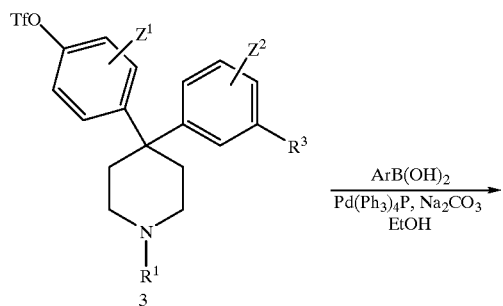

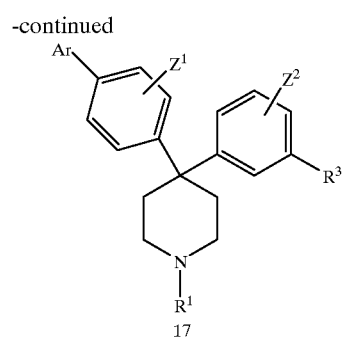

Compounds of the formula 1 wherein $R^2$ is tetrazoyl can be prepared, as illustrated in Scheme 7 below, by conversion of the appropriate triflate of formula 3 into the corresponding nitrile of formula 18. This can be accomplished by reacting the triflate compound with zinc cyanide and a palladium catalyst such as tetrakis triphenylphosphine palladium in a solvent such as dimethylformamide, at a temperature ranging from about 0° C. to about 100° C., preferably at about the reflux temperature. The formation of the tetrazole proceeds by treatment of the resulting nitrile with sodium or trimethylsilylazide and a catalytic amount of tin oxide in a solvent such as dimethylformamide, preferably at about the reflux temperature or toluene, at a temperature ranging from about 20° C. to about the reflux temperature. Alkylation of the tetrazole proceeds by reaction with triethylamine or another trialkylamine base or an alkali metal hydride, alkoxide or carbonate, and with the appropriate compound of the formula $R^6X$ wherein X is a leaving group such as chloro, bromo, iodo, triflate, mesylate or tosylate, in a solvent such as methanol, ethanol, or tetrahydrofuran, at temperatures ranging from about 0° C. to about the reflux temperature, preferably at about room temperature.

SCHEME 7

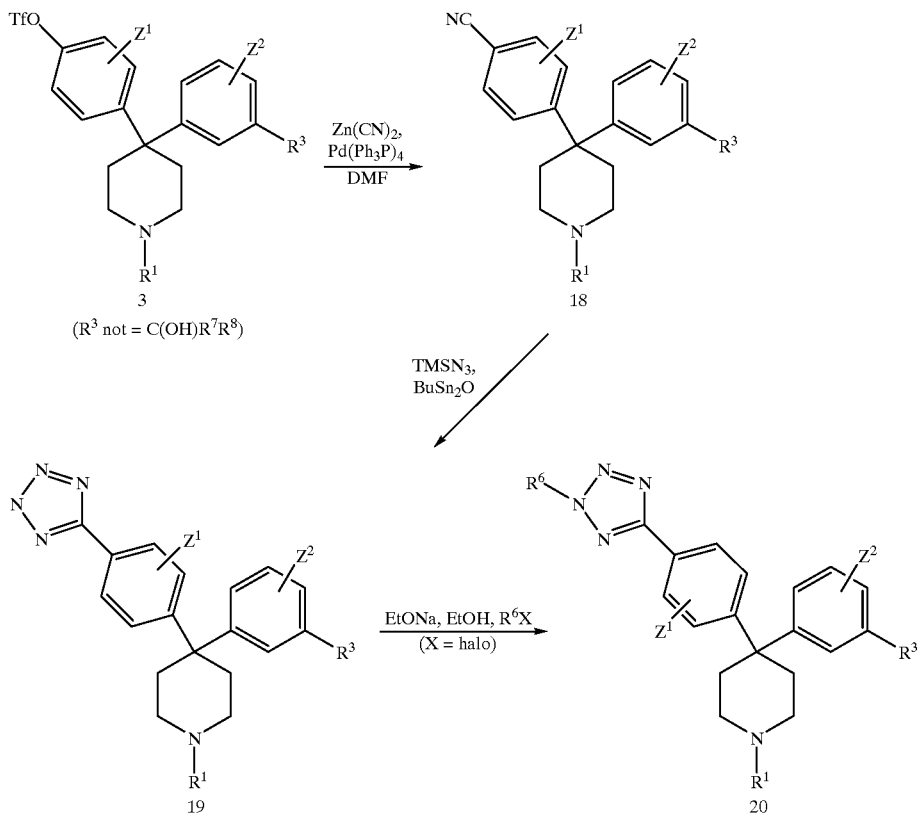

Compounds of the general formula I wherein $R^3$ is fluoro or methoxy and $R^2$ is a heterocycle such as oxazoline or thiazoline can be prepared, as illustrated in Scheme 8, from the appropriate carboxylic acid of formula 20, which can be prepared using conditions identical to those used for the formation of the carboxylic acids of formula 12 (Scheme 5). The carboxylic acid of formula 20 is first converted into the corresponding acid chloride by reaction with oxalyl chloride or thionyl chloride and then treated with the appropriate amino alcohol of the formula $NH_2C(R^5)(R^6)CH_2OH$ or amino thiol of formula $NH_2C(R^5)(R^6)CH_2S$. Conversion to the acid chloride is generally carried out neat or in a solvent such as dichloromethane or dichloroethane, at a temperature from about 0° C. to about the reflux temperature, preferably at about the reflux temperature. Treatment with the appropriate amino alcohol or amino thiol is generally carried out at similar temperatures in a solvent such as dichloromethane or dichloroethame. Dehydrative cyclization using thionyl chloride, neat or in dichloromethane about the reflux temperature, or using trifluoromethane sulfonic anhydride and pyridine or a trialkyl amine such as triethylamine, in dichloromethane, dichloroethane or tetrahydrofuran, at a temperature ranging from about −78° C. to about the reflux temperature, preferably starting at about −78° C. and gradually warming to room temperature, yields the desired compound of formula I. This series of reactions is illustrated in Scheme 8 for the preparation of compounds of the formula I wherein $R^3$ is fluoro or methoxy and $R^2$ is 4,4-dimethyloxazolyl (formula 23 in Scheme 8).

Alternatively, compounds of the formula 23 can be prepared, as illustrated in Scheme 8A, by treatment of the appropriate amide of formula 7 (Scheme 1) with triflic anhydride, pyridine or a trialkylamine base such as triethylamine, and the appropriate amino alcohol or amino thiol, as referred to in the preceding paragraph, in a solvent such as dichloromethane or dichloroethane, at a temperature from about −78° C. to about room temperature, preferably starting at −78° C. and slowly allowing the reaction mixture to warm to room temperature.

SCHEME 8

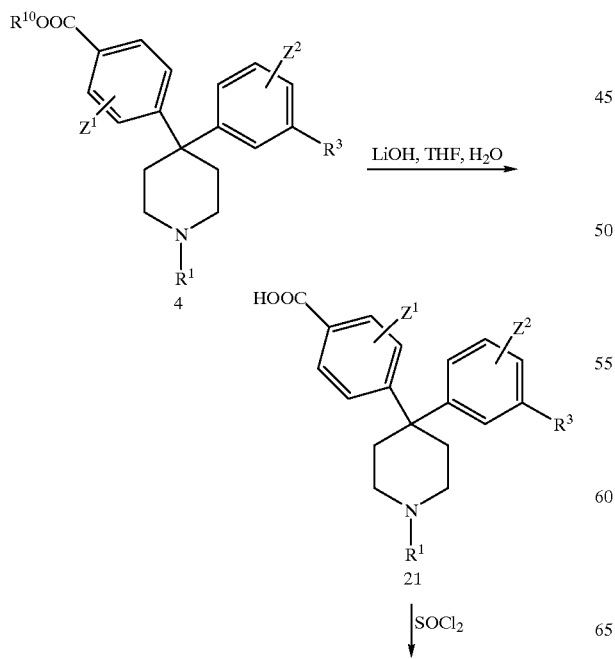

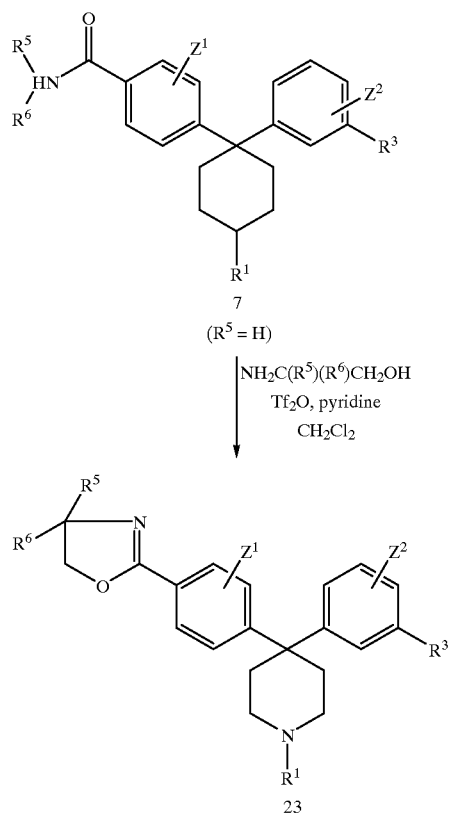

SCHEME 8A

Compounds of the general formula I where $R^3$ is fluoro or methoxy and $R^2$ is a carbinol such as diethyl carbinol (referred to in Scheme 9 as compounds of the formula 24) can be prepared, as illustrated in Scheme 9, by treatment of the ester of formula 4 with an alkyl Grignard or alkyl lithium reagent, in a solvent such as ether or tetrahydrofuran, at a temperature ranging from about −78° C. to about the reflux

SCHEME 9

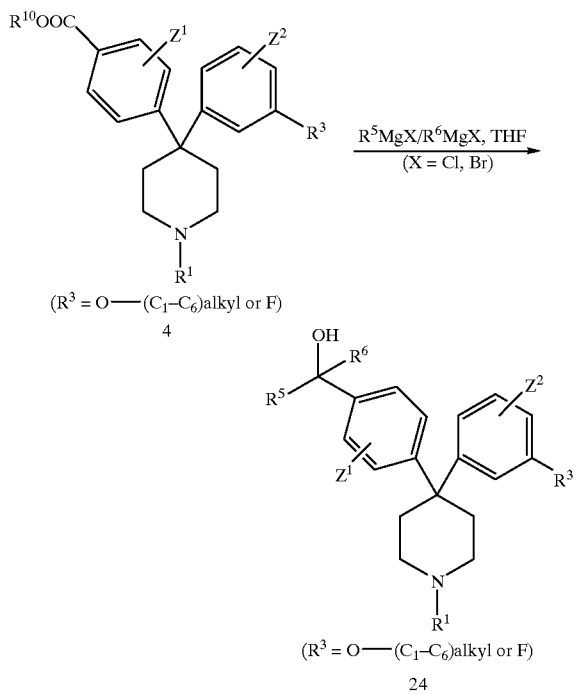

Compounds of the general formula I where $R^2$ is a diazaoxazole ring (e.g., compounds of the formula 27 in Scheme 10) can be prepared, as illustrated in Scheme 10, by treatment of the methyl ester of formula 4 with hydrazine hydrate in methanol, at a temperature from about 0° C. to about the reflux temperature, preferably at about the reflux temperature, to form the hydrazide of formula 25. Subsequent acylation with an acid chloride and pyridine, triethylamine or another trialkylamine in a solvent such as dichloromethane, dichloroethane or toluene, at a temperature from about 0° C. to about the reflux temperature, preferably at about room temperature provides the corresponding compound of formula 26. Cyclization can be accomplished using a reagent combination such as triphenylphospine/iodine and triethylamine or another trialkylamine in a solvent such as tetrahydrofuran, or toluene, at a temperature from about 0° C. to about the reflux temperature, preferably at about room temperature or using triflic anhydride and pyridine or a trialkylamine in dichloromethane, or tetrahydrofuran, at a temperature from about −78° C. to about room temperature, preferably starting at −78° C. and gradually warming to room temperature, or using thionyl chloride in dichloromethane, or neat, at a temperature from about room temperature to about the reflux temperature, preferably at about the reflux temperature, to yield the desired compound of formula 27.

SCHEME 10

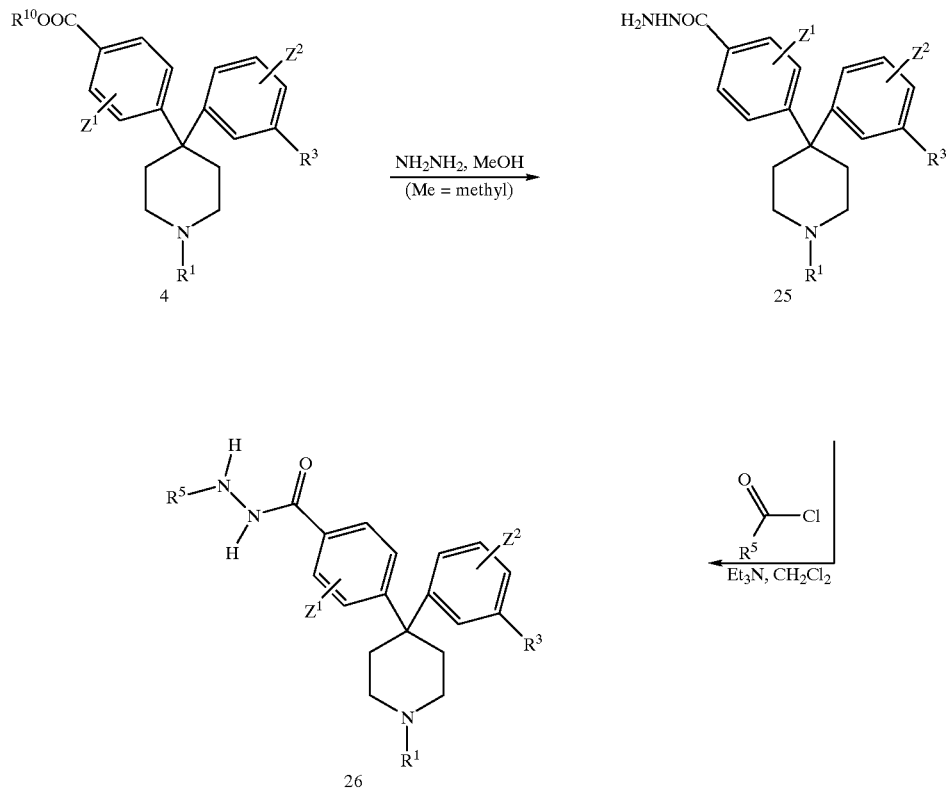

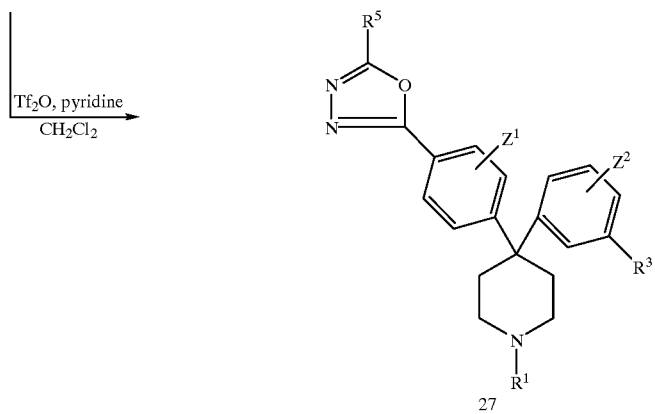

The preferred method of making compounds of the formula I wherein $R^3$ is OH, $NHSO_2R^7$, $C(OH)R^7R^8$ or $C(=O)NHR^7$ is to make the analogous compounds wherein $R^3$ is O—$(C_1-C_6)$alkyl and then derivatize them using standards methods well known in art and illustrated in the foregoing schemes.

The starting materials used in the processes of Schemes 1–10 are either commercially available, known in the literature, or readily obtainable from commercially available or known compounds using methods that are well known in the art or described above.

Unless indicated otherwise, the pressure of each of the above reactions is not critical. Generally, the reactions will be conducted at a pressure from about one to about three atmospheres, preferably at ambient pressure (about one atmosphere).

The preparation of other compounds of the formula I not specifically described in the foregoing experimental section can be accomplished using combinations of the reactions described above that will be apparent to those skilled in the art.

The compounds of the formula I that are basic in nature are capable of forming a wide variety of different salts with various inorganic and organic acids. The acid that can be used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

Compounds of the formula that are acidic in nature are capable of forming base salts with various pharmacologically acceptable cations. These salts are all prepared by conventional techniques. The chemical bases that are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of the formula I and the pharmaceutically acceptable salts thereof (hereinafter, also referred to, collectively, as "the active compounds of the invention") are useful for the treatment of neurodegenerative, psychotropic and drug or alcohol induced deficits and are potent opioid receptor ligands. The active compounds of the invention may therefore be used in the treatment of disorders and conditions, such as those enumerated above, that can be treated by modulatiing binding to an opioid receptor.

The ability of the compounds of formula I to bind to the various opioid receptors and their functional activity at such receptors can be determined as described below. Binding to the delta opioid receptor can be determined using procedures well known in the art, such as those referred to by Lei Fang et al., *J. Pharm. Exp. Ther.*, 268, 1994, 836–846 and Contreras et al., *Brain Research*, 604, 1993, 160–164.

In the description of binding and functional assays that follows, the following abbreviations and terminology are used.

DAMGO is [D-Ala2, N-MePhe4,Gly5-ol]enkephalin).

U69593 is ((5a, 7a, 8b)-(+)-N-methyl-N-(7-[1-pyrrolidinyl]-1-oxasipro[4,5]dec-8-yl)-benzeneacetamide).

SNC-80 is (+)4-[(αR)-α((2S,5R)-4-allyl-2,5-dimethyl-1-piperazinyl)-3-methoxybenzyl]-N,N-diethylbenzamide.

nor BNI is nor-binaltorphimine.

CTOP is 1,2-Dithia-5,8,11,14,17-pentaazacycloeicosane, cyclic peptide derivative DPDPE is [D-en2,D-Pen5]enkephalin).

[3H]-DAMGO, [3H]-U69593, norBNI, and CTOP are all commercially available from DuPont, Amersham International, RBI and DuPont, Amersham International, RBI and DuPont respectively.

[3H]-SNC80 was prepared by Amersham International.

Opioid (mu and kappa) receptor binding assays can be performed in guinea-pig brain membrane preparations. Binding assays can be carried out at 25° C. for 60 minutes in 50 mM Tris (pH 7.4) buffer. [$^3$H]-DAMGO(2 nM) and [$^3$H]-U-69,593 (2 nM) can be used to label mu and kappa receptor binding sites, respectively. The protein concentration can be approximately 200 μg/well. Non-specific binding can be defined with 10 μM naloxone.

Delta receptor binding assays can be performed in a stable line of CHO cells expressing the human delta receptor. The binding assay can be carried out at 25° C. for 120 minutes in 50 mM Tris (pH 7.4) buffer. [$^3$H]-SNC-80 can be used to label delta receptor binding sites. The protein concentration can be approximately 12.5 μg/well. Non-specific binding can be defined with 10 μM naltrexone.

The binding reaction can be terminated by rapid filtration through glass fibre filters, and the samples can be washed with ice-cold 50 mM Tris buffer (pH 7.4).

Agonist activity at the delta, mu and kappa opioid receptors can be determined as follows.

Opioid (delta, mu and kappa) activity is studied, as described below, in two isolated tissues, the mouse deferens (MVD)(δ) and the guinea-pig myentric plexus with attached longitudinal muscle (GPMP) (μ and k).

MVD (DC1 strain, Charles River, 25–35 g) are suspended in 15 ml organ baths containing Mg$^{++}$ free Krebs' buffer of the following composition (mM): NaCl, 119; KCl, 4.7; NaHCO$_3$, 25; KH$_2$PO$_4$, 1.2; CaCl$_2$, 2,5 and glucose, 11. The buffer is gassed with 95% O$_2$ and 5% CO$_2$. The tissues are suspended between platinum electrodes, attached to an isometric transducer with 500 mg tension and stimulated with 0.03 Hz pulses of 1-msec pulse-width at supramaximal voltage. IC$_{50}$ values are determined by the regression analysis of concentration-response curves for inhibition of electrically-induced contractions in the presence of 300 nM of the mu-selective antagonist CTOP. This test is a measure of δ agonism.

Guinea-pig (Porcellus strain, male, 450–500 g, Dunkin Hartley) myentric plexus with attached longitudinal muscle segments are suspended with 1 g of tension in Krebs' buffer and stimulated with 0.1 Hz pulses of 1-msec pulse-width at supramaximal voltage. Mu functional activity is determined in the presence of 10 nM nor-BNI with 1 μM of the mu selective agonist, DAMGO, added to the bath at the end of the experiment to define a maximal response. This test is a measure of mu agonism.

Kappa functional activity is determined in the presence of and 1 μM CTOP with 1 μM of the kappa selective agonist U-69,593 added at the end of the experiment to define a maximal response. All inhibitions of twitch height for test compounds are expressed as a percentage of the inhibition obtained with the standard agonist and the corresponding IC$_{50}$ values determined.

The following procedure can be used to determine the activity of the therapeutic agents of this invention as agonists and as antagonists of delta opioid receptors.

Cell Culture: Chinese hamster ovary cells expressing the human delta opioid receptor are passaged twice weekly in Hamis F-12 media with L-glutamine containing 10% fetal bovine serum and 450 μg/mL hygromycin. Cells are prepared for assays 3 days prior to the experiment. 15 mL of 0.05% trypsin/EDTA is added to a confluent triple flask, swirled and decanted to rinse. 15 mL of 0.05% trypsin/EDTA is again added, and the flask is placed into a 37C incubator for 2 minutes. Cells are removed from the flask by banking, and supernatant poured off into a 50 mL tube. 30 mL of media is then added to the flask to stop the action of the trypsin, and then decanted into the 50 mL tube. Tube is then centrifuged for 5 minutes at 1000 rpm, media decanted, and the pellet resuspended into 10 mL of media. Viability of the cells is assessed using trypan blue, the cells counted and plated out into 96 well poly-D-lysine coated plates at a density of 7,500 cells/well.

Antagonist Test Plate: Cells plated 3 days prior to assay are rinsed twice with PBS. The plates are placed into a 37C water bath. 50 μL of assay buffer (PBS, dextrose 1 mg/mL, 5 mM MgC12, 30 mM HEPES, 66.7 μg/mL of IBMX) is then added to designated wells. Fifty microliters of appropriate drug is then added to designated wells, and timed for 1 minute. Fifty microliters of 10 μM forskolin+0.4 nM DPDPE (final assay concentration is 5 μM forskolin, 0.2 nM DPDPE) is then added to appropriate wells, and timed for 15 minutes. The reaction is stopped by the addition of 10 μL of 6N perchloric acid to all wells. To neutralize, 13 μL of 5N KOH is added to all wells, and to stabilize 12 μL of 2M Tris, pH 7.4 is added to all wells. Mix by shaking on an orbital shaker for 10 minutes, and centrifuge at setting 7 for 10 minutes. Alliquot into 3H plate.

Agonist Test Plate: Cells plated 3 days prior to assay are rinsed twice with PBS. The plates are placed into a 37° C. water bath. Fifty microliters of assay buffer (PBS, dextrose 1 mg/mL, 5 mM MgCl$_2$, 30 mM HEPES, 66.7 μg/mL of IBMX) is then added to designated wells. Fifty microliters of appropriate drug+10 μM forskolin (final assay concentration is 5 μM forskolin) is then added to all wells, and timed for 15 minutes. The reaction is then stopped by the addition of 10 μL of 6N perchloric acid to all wells. To neutralize, 13μ of 5N KOH is added to all wells, and to stablize 12 μL of 2M Tris, pH 7.4 is added to all wells. Mix by shaking on an orbital shaker for 10 minutes, and centrifuge at setting 7 for 10 minutes. Alliquot into 3H plate.

Both test plates are placed into an Amersham 3H cAMP binding kit overnight, and harvested onto GF/B filters previously soaked in 0.5% PEI with a Skatron using 50 mM Tris HCl pH 7.4 at 4° C. Filtermats can be air-dried overnight then place in bags with 20 ml Betaplate scintillation cocktail and counted on a Betaplate counter for 60 sec per sample. Data can be analyzed using Excel.

The compositions of the present invention may be formulated in a conventional manner using one or more pharmaceutically acceptable carriers. Thus, the active compounds of the invention may be formulated for oral, buccal, transdermal (e.g., patch), intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

In general, a therapeutically effective daily oral or intravenous dose of the compounds of formula (I) and their salts is likely to range from 0.001 to 50 mg/kg body weight of the subject to be treated, preferably 0.1 to 20 mg/kg. The compounds of the formula (I) and their salts may also be administered by intravenous infusion, at a dose which is likely to range from 0.001–10 mg/kg/hr.

Tables or capsules of the compounds may be administered singly or two or more at a time as appropriate. It is also possible to administer the compounds in sustained release formulations.

The physician will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

Alternatively, the compounds of the formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stablisers and preservatives as may be required.

The following Examples illustrate the preparation of the compounds of the present invention. Commercial reagents were utilized without further purification. All NMR data were recorded at 250, 300 or 400 MHz in deuterochloroform unless otherwise specified and are reported in parts per million ($\delta$) and are referenced to the deuterium lock signal from the sample solvent. All non-aqueous reactions were carried out in dry glassware with dry solvents under an inert atmosphere for convenience and to maximize yields. All reactions were stirred with a magnetic stirring bar unless otherwise stated. Unless otherwise stated, all mass spectra were obtained using chemical impact conditions. Ambient or room temperature refers to 20–25° C.

EXAMPLE 1

N,N-DIETHYL-4-[4-(3-HYDROXY-PHENYL)-PIPERIDIN-4-YL]-BENZAMIDE

A. 1-Benzyl-4-(3-methoxy-phenyl)-piperidin-4-ol

To a solution of 3-bromoanisole (20.9 mL, 0.16 mmol) in THF (150 mL) at −78° C. under a nitrogen atmosphere was added n-BuLi (66 mL, 0.16 mmol, 2.5M in hexanes) over 10 min. The resulting slurry was stirred at −78° C. for 1 hour. To the mixture was added a solution an N-benzyl-4-piperidinone (27.8 mL, 0.15 mmol) in THF (30 mL). The reaction was stirred at −78° C. for 2 hours and at room temperature for 10 hours. The mixture was poured slowly over ice-water (100 mL) and the aqueous layer was washed with EtOAc (3×50 mL). The combined organic extracts were dried (MgSO$_4$) and concentrated. The crude residue was purified by flash chromatography with hexanes/EtOAc (3:1) to afford 42.2 g of the alcohol (95% yield). $^1$HNMR (400 MHz, CDCl$_3$) $\delta$ 7.35–7.22 (comp, 6H), 7.07–7.04 (comp, 2H), 6.80–6.77 (m, 1H), 3.80 (s, 1H), 3.58 (s, 1H), 2.79 (d, 2H), 2.48 (t, 2H), 2.19–2.13 (comp, 2H), 1.72 (dd, 2H), 1.58 (s, 1H); MS (M+1) 298.3.

B. 4-[1-Benzyl-4-(3-methoxy-phenyl)-piperidin-4-yl]-phenol

To a solution of 1-Benzyl-4-(3-methoxy-phenyl)-piperidin-4-ol (21.7 g, 73.1 mmol) in (CH$_2$)$_2$Cl$_2$ (200 mL) was added phenol (20.7 g, 220 mmol) followed by portionwise addition (highly exothermic) of AlCl$_3$ (29.3 g, 200 mmol). The reaction mixture was heated to reflux for 10 hours. The mixture was cooled to room temperature and was slowly poured into a mixture of crushed ice (50 mL) and 30% aq. NH$_4$OH (120 mL). The mixture was stirred vigorously for 20 minutes and was then filtered through celite. The celite cake was washed with CH$_2$Cl$_2$ (200 mL). The organic layer was separated and the aqueous layer was washed with CH$_2$Cl$_2$ (3×100 mL). The combined organic layers were dried (MgSO$_4$) and concentrated. The crude residue was purified by flash chromatography with hexanes/EtOAc (1:1) to afford 20.1 g (73% yield) of 4-[1-Benzyl-4-(3-methoxy-phenyl)-piperidin-4-yl]-phenol. $^1$HNMR (400 MHz, CD$_3$OD) $\delta$ 7.28–7.20 (comp, 5H), 7.14 (t, 1H), 7.07 (d, 2H), 6.83 (d, 2H), 6.76 (s, 1H), 6.70–6.60 (comp, 3H), 3.69 (s, 3H), 3.39 (s, 2H), 2.50–2.40 (comp, 4H), 2.39–2.29 (comp, 4H); MS (M+1) 374.2.

C. Trifluoro-methanesulfonic acid 4-[1-benzyl-4-(3-methoxy-phenyl)-piperidin-4-yl]-phenyl ester To a slurry of 4-[1-Benzyl-4-(3-methoxy-phenyl)-piperidin-4-yl]-phenol (22.3 g, 59.8 mmol) in $CH_2Cl_2$ (200 mL) at 0° C. was added pyridine (9.26 mL, 89.7 mmol) followed by dropwise addition of triflic anhydride (15.1 mL, 89.7 mmol) over 10 minutes. The reaction mixture was stirred at 0° C. for 1 hour and at room temperature for 2 hour. The solution was then cooled to 0° C. and 40 mL of cold saturated aqueous $NaHCO_3$ were added. The organic layer was separated and the aqueous layer was washed with $CH_2Cl_2$ (3×50 mL). The combined organic layers were dried ($MgSO_4$) and concentrated. The crude residue was purified by flash chromatography with hexanes/EtOAc (3:1) to afford 22.1 g (75% yield) of trifluoro-methanesulfonic acid 4-[1-benzyl-4-(3-methoxy-phenyl)-piperidin-4-yl]-phenyl ester. $^1$HNMR (400 MHz, $CDCl_3$) δ 7.32–7.20 (comp, 8H), 7.14 (d, 2H), 6.84 (d, 1H), 6.81 (s, 1H), 6.72 (dd, 1H), 3.77 (s, 3H), 3.41 (s, 2H), 2.55–2.38 (comp, 8H); MS (M+1) 505.9.

D. 4-[1-Benzyl-4-(3-methoxy-phenyl)-piperidin-4-yl]-1-benzoic acid methyl ester

To a solution of trifluoro-methanesulfonic acid 4-[1-benzyl-4-(3-methoxy-phenyl)-piperidin-4-yl]-phenyl ester (10.0 g, 19.8 mmol) in a Parr pressure bottle in MeOH (69 mL) were added DMSO (62 mL) and triethylamine (21.8 mL, 157 mmol). To the reaction mixture were added palladium acetate (2.2 g, 9.1 mmol) and 1,3-bis(diphenylphosphino)propane (3.75 g, 9.1 mmol). The mixture was shaken under 40 psi of CO at 70° C. for 4 hours. The reaction mixture was cooled to room temperature and was diluted with diethyl ether (600 mL). The ether layer was washed with water (5×60 mL), dried ($MgSO_4$) and concentrated. The crude residue was purified by flash chromatography with hexanes/EtOAc (1:1) to afford 6.9 g (85% yield) of 4-[1-Benzyl-4-(3-methoxy-phenyl)-piperidin-4-yl]-benzoic acid methyl ester. $^1$HNMR (400 MHz, $CDCl_3$) δ 7.91 (d, 2H), 7.32 (d, 2H), 7.28–7.16 (comp, 6H),), 6.82 (d, 1H), 6.79 (s, 1H), 6.68 (dd, 1H), 3.86 (s, 3H), 3.74 (s, 3H), 3.38 (s, 2H), 2.47–2.44 (comp, 8H); MS (M+1) 416.2.

E. 4-[1-Benzyl-4-(3-methoxy-phenyl)-piperidin-4-yl]-N,N-diethyl-benzamide

To a solution of diethyl amine (1.88 mL, 18.2 mmol) in $CH_2ClCH_2Cl$ (7 mL) at room temperature was added a trimethylaluminum (9.1 mL, 18.2 mmol, 2M in hexanes) dropwise. The reaction mixture was stirred at room temperature for 1 hour. A solution of of 4-[1-Benzyl-4-(3-methoxy-phenyl)-piperidin-4-yl]-benzoic acid methyl ester (1.51 g, 3.64 mmol) in $(CH_2)_2Cl_2$ (6 mL) was added and the reaction mixture was heated to reflux for 14 hours. The solution was then cooled 0° C. and sat. aqueous $NaHCO_3$ (15 mL) was added dropwise. The mixture was filtered through celite. The celite cake was washed with $CH_2Cl_2$ (40 mL). The organic layer was separated and the aqueous layer was washed with $CH_2Cl_2$ (3×30 mL). The combined organic layers were dried ($MgSO_4$) and concentrated. The crude residue was purified by flash chromatography with EtOAc to afford 1.4 g (84% yield) of 4-[1-Benzyl-4-(3-methoxy-phenyl)-piperidin-4-yl]-N,N-diethyl-benzamide. $^1$HNMR (400 MHz, $CDCl_3$) δ 7.28–7.16 (comp, 10H), 6.84–6.80 (comp, 2H), 6.68 (dd, 1H), 3.74 (s, 3H), 3.52–3.48 (comp, 2H), 3.39 (s, 2H), 3.24–3.21 (comp, 2H), 2.47–2.42 (comp, 8H), 1.22–1.20 (comp, 3H), 1.19–1.16 (comp, 3H); MS (M+1) 457.2.

F. N,N-Diethyl-4-[4-(3-hydroxy-phenyl)-piperidin-4-yl]-benzamide

To a solution of 4-[1-Benzyl-4-(3-hydroxy-phenyl)-piperidin-4-yl]-N,N-diethylbenzamide (1.11 g, 2.49 mmol) in acetic acid (8 mL) in a Parr pressure bottle was added $Pd(OH)_2$ (10% on carbon, 0.4 g). The reaction mixture was shaken under 50 psi of $H_2$ for 20 hours. The reaction mixture was then filterd through celite. The celite cake was washed with EtOAc (250 mL) and the organic layer was concentrated to remove the acetic acid. The residue was partitioned between $CH_2Cl_2$ (10 mL) and 30% aqueous $NH_4OH$ (10 mL). The organic layer was separated and the aqueous layer was washed with $CH_2Cl_2$ (3×20 mL). The combined organic layers were dried ($MgSO_4$) and concentrated to afford 0.74 g of N,N-Diethyl-4-[4-(3-hydroxy-phenyl)-piperidin-4-yl]-benzamide (83% yield) which was used with no further purification. $^1$HNMR (400 MHz, $CD_3CO_2D$) δ 7.24–7.06 (comp, 5H), 6.75 (s, 1H), 6.70 (d, 1H), 6.58 (d, 1H), 3.49–3.40 (comp, 2H), 3.21–3.15 (comp, 2H), 2.90–2.85 (comp, 4H), 2.39–2.33 (comp, 4H), 1.20–1.15 (comp, 3H), 1.08–1.02 (comp, 3H); MS (M+1) 353.2.

The following compounds were made using the procedures set forth above in Example 1, starting with a compound analogous to the title compound of Example 1A wherein $R^3$ is fluro or methoxy, and adding the appropriate amine reactant in the procedure of Example 1E.

4-[1-Benzyl-4-(3-methoxy-4-methyl-phenyl)-piperidin-4-yl]-N,N-diethylbenzamide. $^1$HNMR (400 MHz, $CDCl_3$) δ 7.01 (d, 1H), 6.68 (d, 1H), 6.61 (s, 1H), 3.70 (s, 3H), 3.41 (s, 2H), 2.18 (s, 3H); MS (M+1) 471.2.

4-[1-Benzyl-4-(3-methoxy-phenyl)-piperidin-4-yl]-N-methyl-benzamide. $^1$HNMR (400 MHz, CDCl3) d (400 MHz, $CDCl_3$) δ 7.62(d, 2H), 6.79 (d, 1H), 6.66 (d, 1H), 6.04 (br, 1H), 3.77 (s, 3H), 2.99 (d, 3H); MS (M+1) 415.2.

4-[1-Benzyl-4-(3-methoxy-phenyl)-piperidin-4-yl]-2-fluoro-N,N-dimethyl-benzamide. $^1$HNMR (400 MHz, $CDCl_3$) δ 7.09 (d, 1H), 6.95 (d, 1H), 6.71 (d, 1H), 3.79 (s, 3H), 3.09 (s, 3H), 2.89 (s, 3H); MS (M+1) 447.2.

4-[1-Benzyl-4-(3-methoxy-phenyl)-piperidin-4-yl]-N-ethyl-N-methyl-benzamide. $^1$HNMR (400 MHz, $CDCl_3$) δ 6.85–6.79 (comp, 2H), 6.68 (d, 1H), 3.79 (s, 3H), 3.4 (s, 2H), 3.1–2.82 (comp, 3H); MS (M+1) 443.3.

4-[1-Benzyl-4-(3-fluoro-phenyl)-piperidin-4-yl]-N,N-diethyl-benzamide. $^1$HNMR (400 MHz, $CDCl_3$) δ 7.02 (d, 1H), 6.88 (d, 1H), 6.81 (t, 1H), 2.62–2.22 (comp, 8H); MS (M+1) 445.2.

EXAMPLE 2

GENERAL PROCEDURE FOR REDUCTIVE ALKYLATION OF N,N-DIETHYL-4-[4-(3-HYDROXY, FLUORO OR METHOXY-PHENYL)-PIPERIDIN-4-YL]-BENZAMIDES

To a solution of N,N-Diethyl-4-[4-(3-hydroxy-phenyl)-piperidin-4-yl]-benzamide (1 equivalent) in $CH_2Cl_2$ (0.4M) was added the aldehyde (1.2 equivalents) followed by addition of acetic acid (1.2 equivalents) and $NaBH(OAc)_3$ (1.5 equivalents). The reaction mixture was stirred at room temperature for 16 hours. The mixture was then partitioned between equal volumes of $CH_2Cl_2$ and sat. aqueous $NaHCO_3$. The organic layer was separated and the aqueous layer was washed with $CH_2Cl_2$ (3×). The combined organic layers were dried ($MgSO_4$) and concentrated. Purification by flash chromatography afforded the desired tertiary amines in yields ranging from 60–95%.

The following compounds were made using the above procedure of Example 2, starting with a diarylsubstituted pyridine wherein $R^3$ is fluoro or methoxy and $R^2$ is the appropriate amide group.

{4-[1-(3-Cyclohexyl-propyl)-4-(3-methoxy-phenyl)-piperidin-4-yl]-phenyl}-morpholin-4-yl-methanone. $^1$HNMR (400 MHz, CDCl$_3$) δ 6.82 (d, 1H), 6.79 (s, 1H), 6.71 (d, 1H), 3.75 (s, 3H), 1.79–1.61 (comp, 8H); MS (M+1) 505.3.

{4-[1-Hexyl-4-(3-methoxy-phenyl)-piperidin-4-yl]-phenyl}-morpholin-4-yl-methanone. $^1$HNMR (400 MHz, CDCl$_3$) δ 6.81 (d, 1H), 6.79 (d, 1H), 6.68 (d, 1H), 3.75 (s, 3H), 1.46–1.41 (comp, 2H), 0.84 (t, 3H); MS (M+1) 465.3.

N,N-Diethyl-4-[4-(3-methoxy-phenyl)-1-(2-phenyl-propyl)-piperidin-4-yl]-benzamide. $^1$HNMR (400 MHz, CDCl$_3$) δ 6.82–6.79 (comp, 2H), 6.66 (d, 1H), 3.77 (s, 3H), 2.85 (m, 1H), 1.22 (d, 3H); MS (M+1) 485.3.

N,N-Diethyl-4-[1-hexyl-4-(3-methoxy-phenyl)-piperidin-4-yl]-benzamide. $^1$HNMR (400 MHz, CDCl$_3$) δ 7.18 (t, 1H), 6.82–6.80 (comp, 2H), 6.67 (d, 1H), 3.74 (s, 3H), 3.57–3.42 (comp, 2H), 2.26–2.20 (comp, 2H), 0.84 (t, 3H); MS (M+1) 451.3.

4-[1-(3-Cyclohexyl-propyl)-4-(3-methoxy-phenyl)-piperidin-4-yl]-N,N-diethyl-benzamide. $^1$HNMR (400 MHz, CDCl$_3$) δ 6.81 (d, 1H), 6.76 (s, 1H), 6.68 (d, 1H), 3.73 (s, 3H), 3.23–3.19 (comp, 2H), 2.47–2.39 (comp, 2H); MS (M+1) 491.3.

4-[1-(3-Cyclohexyl-propyl)-4-(3-fluoro-phenyl)-piperidin-4-yl]-N,N-diethyl-benzamide. $^1$HNMR (400 MHz, CDCl$_3$) δ 7.01 (d, 1H), 6.86 (d, 1H), 6.82 (t, 1H), 3.59–3.4 (comp, 2H), 2.26–2.20 (comp, 2H); MS (M+1) 479.3

N,N-Diethyl-4-[4-(3-fluoro-phenyl)-1-(3-phenyl-propyl)-piperidin-4-yl]-benzamide. $^1$HNMR (400 MHz, CDCl$_3$) δ 7.02 (d, 1H), 6.69 (d, 1H), 6.81 (t, 1H), 3.33–3.19 (comp, 2H), 2.50 (t, 2H), 1.83–1.71 (comp, 2H); MS (M+1) 473.2.

N,N-Diethyl-4-[4-(3-fluoro-phenyl)-1-methyl-piperidin-4-yl]-benzamide. $^1$HNMR (400 MHz, CDCl$_3$) δ 7.02 (d, 1H), 6.85 (d, 1H), 2.61–2.41 (comp, 8H), 2.26 (s, 3H); MS (M+1) 369.2.

N,N-Diethyl-4-[4-(3-fluoro-phenyl)-1-hexyl-piperidin-4-yl]-benzamide. $^1$HNMR (400 MHz, CDCl$_3$) δ 7.02 (d, 1H), 6.92–6.80 (comp, 2H), 2.52–2.40 (comp, 2H), 1.63–1.45 (comp, 2H), 0.79 (t, 3H); MS (M+1) 439.3.

N,N-Diethyl-4-[4-(3-fluoro-phenyl)-1-(4-methyl-benzyl)-piperidin-4-yl]-benzamide. $^1$HNMR (400 MHz, CDCl$_3$) δ 7.08 (d, 2H), 7.02 (d, 1H), 6.91 (d, 1H), 3.36 (s, 2H), 2.59–2.38 (comp, 8H), 2.31 (s, 3H); MS (M+1) 459.2.

N,N-Diethyl-4-[4-(3-fluoro-phenyl)-1-(2-methyl-pentyl)-piperidin-4-yl]-benzamide. $^1$HNMR (400 MHz, CDCl$_3$) δ 7.03 (d, 1H), 6.92 (d, 1H), 6.85 (t, 1H), 3.59–3.41 (comp, 2H), 1.75–1.59 (comp, 2H); MS (M+1) 439.3.

N,N-Diethyl-4-[4-(3-fluoro-phenyl)-1-(3-methyl-butyl)-piperidin-4-yl]-benzamide. $^1$HNMR (400 MHz, CDCl$_3$) δ 7.02 (d, 1H), 6.93 (d, 1H), 6.83 (t, 1H), 3.31–3.19 (comp, 2H), 1.58-1.43-(m, 1H), 1.39–1.29 (comp, 2H), 0.86 (d, 6H); MS (M+1) 425.3.

EXAMPLE 3

ALKYLATION OF N,N-DIETHYL-4-[4-(3-METHOXY-PHENYL)-PIPERIDIN-4-YL]-BENZAMIDE

To a solution of N,N-Diethyl-4-[4-(3-methoxy-phenyl)-piperidin-4-yl]-benzamide (1 equivalent) in DMF (0.5M) was added K$_2$CO$_3$ (3–10 equivalents) and the alkyl or heteroaryl halide (1–5 equivalents). The reaction mixture was stirred at 60–120° C. for 3–16 hours. The mixture was then cooled to room temperature and filtered. The filtrate was diluted with diethyl ether and the ether layer was washed with brine. The organic phase was dried (MgSO$_4$) and concentrated. Purification by flash chromatography afforded the desired amines in yields ranging from 30–85%.

The following compounds were made using a procedure analogous to that of Example 3, starting with the appropriate amide group.

4-[1-Allyl-4-(3-methoxy-phenyl)-piperidin-4-yl]-N,N-diethyl-benzamide. $^1$HNMR (400 MHz, CDCl3) d 7.19 (t, 1H), 6.84–6.80 (comp, 2H), 6.69 (d, 1H), 5.88–5.79 (m, 1H), 5.15–5.10 (comp, 2H), 3.75 (s, 3H), 2.95–2.87 (comp, 2H); MS (M+1) 407.2.

4-[1-Cyclopropylmethyl-4-(3-methoxy-phenyl)-piperidin-4-yl]-N,N-diethyl-benzamide. $^1$HNMR (400 MHz, CDCl3) d 7.18 (t, 1H), 6.85–6.79 (comp, 2H), 6.68 (d, 1H), 3.74 (s, 3H), 2.21–2.10 (comp, 2H), 1.88–1.78 (comp, 1H), 1.51–1.39 (comp, 2H); MS (M+1) 421.2.

N,N-Diethyl-4-[4-(3-methoxy-phenyl)-3,4,5,6-tetrahydro-2H-[1,2']bipyridinyl-4-yl]-benzamide. $^1$HNMR (400 MHz, CDCl3) d 8.15 (d, 1H), 7.44 (t, 1H), 6.88–6.84 (comp, 2H), 6.69 (d, 1H), 6.64 (d, 1H), 6.57 (t, 1H), 3.75 (s, 3H), 3.71–3.56 (comp, 4H), 2.58–2.40 (comp, 4H); MS (M+1) 444.4.

N,N-Diethyl-4-[4-(3-methoxy-phenyl)-1-pyrimidin-2-yl-piperidin-4-yl]-benzamide. $^1$HNMR (400 MHz, CDCl3) d 8.27 (d, 2H), 6.88–6.80 (comp, 2H), 6.68 (d, 1H), 6.44 (t, 1H), 3.95–3.75 (comp, 4H), 3.74 (s, 3H), 3.30–3.19 (comp, 2H); MS (M+1) 445.4.

EXAMPLE 4

DEPROTECTION OF METHYL ARYL ETHERS

To a solution of methyl ether (1 equivalent) in CH$_2$Cl$_2$ (0.4M) at −78° C. was added a solution of boron tribromide (1–5 equivalents) in CH$_2$Cl$_2$ (1.0 M) dropwise. The reaction mixture was stirred at −78° C. for 1 hour was warmed to room temperature and stirred for an additional 4–6 hour. The mixture was quenched with slow addition of water and was brought to pH 8 with a saturated water/NH$_4$OH solution. The aqueous layer was washed with CH$_2$Cl$_2$. The organic phase was dried (MgSO$_4$) and concentrated. Purification by flash chromatography afforded the desired phenols in yields ranging from 60–95%.

Alternatively, the methyl ethers were deprotected with sodium hydride and ethane thiol in DMF as follows:

To a suspension of NaH (10 equivalents) in DMF (0.2M) at room temperature was added ethane thiol (10 equivalents) dropwise. The mixture was stirred for 5 minutes. To the reaction mixture was added a solution of the methyl ether (1 equivalent) in DMF (0.2M). The mixture was heated to 120° C. for 10–16 hours. The reaction was cooled to room temperature and was quenched with water. The mixture was diluted with diethyl ether and the organic layer was washed with brine. The organic phase was dried (MgSO$_4$) and concentrated. Purification by flash chromatography afforded the desired phenols in yields ranging from 60–95%.

The following compounds were made using the procedure of Example 4.

N,N-Diethyl-4-[4-(3-hydroxy-phenyl)-1-methyl-piperidin-4-yl]-benzamide. $^1$HNMR (400 MHz, CDCl$_3$) δ 6.72–6.67 (comp, 2H), 6.61 (d, 1H), 3.51–3.41 (comp, 2H), 2.24–3.19 (comp, 2H), 1.24 (s, 3H); MS (M+1) 367.1.

4-[1-Allyl-4-(3-hydroxy-phenyl)-piperidin-4-yl]-N,N-diethyl-benzamide. $^1$HNMR (400 MHz, CDCl$_3$) δ 6.74–6.65 (comp, 2H), 6.64 (d, 1H), 5.99–5.80 (m, 1H), 5.22–5.15 (comp, 2H), 3.35–3.19 (comp, 2H), 3.05–2.95 (comp, 2H); MS (M+1) 393.2.

4-[1-Benzyl-4-(3-hydroxy-phenyl)-piperidin-4-yl]-N,N-diethyl-benzamide. $^1$HNMR (400 MHz, CDCl$_3$) δ 6.78 (d, 1H), 6.63 (d, 1H), 6.61 (s, 1H), 3.50 (comp, 2H), 3.42 (s, 2H), 1.19–1.01 (comp, 3H); MS (M+1) 443.2.

4-[1-Cyclopropylmethyl-4-(3-hydroxy-phenyl)-piperidin-4-yl]-N,N-diethyl-benzamide. $^1$HNMR (400 MHz, CDCl$_3$) δ 6.90 (s, 1H), 6.78–6.61 (comp, 2H), 3.30–3.19 (comp, 2H), 0.69–0.64 (comp, 2H), 0.33–0.30 (comp, 2H); MS (M+1) 407.2.

N,N-Diethyl-4-[4-(3-hydroxy-phenyl)-1-phenethyl-piperidin-4-yl]-benzamide. $^1$HNMR (400 MHz, CDCl$_3$) δ 6.79 (d, 1H), 6.69 (s, 1H), 6.63 (d, 1H), 2.81–2.68 (comp, 2H); MS (M+1) 457.2

N,N-Diethyl-4-[4-(3-hydroxy-phenyl)-1-thiazol-2-ylmethyl-piperidin-4-yl]-benzamide. $^1$HNMR (400 MHz, CDCl$_3$) δ 7.69 (d, 1H), 7.27 (d, 1H), 7.09 (t, 1H), 6.77 (d, 1H), 6.68 (s, 1H), 6.59 (d, 1H), 3.75 (s, 2H); MS (M+1) 450.1.

N,N-Diethyl-4-[4-(3-hydroxy-phenyl)-1-thiophen-2-ylmethyl-piperidin-4-yl]-benzamide. $^1$HNMR (400 MHz, CDCl$_3$) δ 6.94–6.91 (comp, 2H), 6.78 (d, 1H), 6.64–6.60 (comp, 2H), 3.62 (s, 2H), 3.55–3.45 (comp, 2H); MS (M+1) 449.1.

N,N-Diethyl-4-[4-(3-hydroxy-phenyl)-1-(4-methyl-benzyl)-piperidin-4-yl]-benzamide. $^1$HNMR (400 MHz, CDCl$_3$) δ 6.98 (d, 2H), 6.79 (d, 1H), 6.62 (d, 1H), 6.46 (s, 1H), 3.32 (s, 3H), 2.29 (s, 3H); MS (M+1) 457.2.

4-[1-Butyl-4-(3-hydroxy-phenyl)-piperidin-4-yl]-N,N-diethyl-benzamide. $^1$HNMR (400 MHz, CDCl$_3$) δ 6.74 (d, 1H), 6.66 (s, 1H), 6.61 (d, 1H), 1.48–1.39 (comp, 2H), 0.85 (t, 3H); MS (M+1) 409.3.

4-[1-(3-Cyclohexyl-propyl)-4-(3-hydroxy-phenyl)-piperidin-4-yl]-N,N-diethyl-benzamide. $^1$HNMR (400 MHz, CDCl$_3$) δ 6.78 (s, 1H), 6.72–6.66 (comp, 2H), 1.71–1.54 (comp 7H), 0.83–0.72 (comp, 2H); MS (M+1) 477.3.

N,N-Diethyl-4-[1-hexyl-4-(3-hydroxy-phenyl)-piperidin-4-yl]-benzamide. $^1$HNMR (400 MHz, CDCl$_3$) δ 6.75 (d, 1H), 6.70 (s, 1H), 6.64 (d, 1H), 1.59–1.41 (comp, 2H), 0.84 (t, 3H); MS (M+1) 437.3.

N,N-Diethyl-4-[4-(3-hydroxy-phenyl)-1-(3-methyl-butyl)-piperidin-4-yl]-benzamide. $^1$HNMR (400 MHz, CDCl$_3$) δ 6.76 (s, 1H), 6.71 (d, 1H), 6.67 (d, 1H), 0.87 (d, 3H); MS (M+1) 423.3

N,N-Diethyl-4-[4-(3-hydroxy-phenyl)-1-isobutyl-piperidin-4-yl]-benzamide. $^1$HNMR (400 MHz, CDCl$_3$) δ 6.74 (d, 1H), 6.69 (s, 1H), 6.60 (d, 1H), 2.11–2.02 (comp, 2H), 1.80–1.73 (m, 1H), 0.86 (d, 6H); MS (M+1) 409.3.

N,N-Diethyl-4-[4-(3-hydroxy-phenyl)-1-(4-isopropyl-benzyl)-piperidin-4-yl]-benzamide. $^1$HNMR (400 MHz, CDCl$_3$) δ 7.08 (t, 1H), 7.01 (d, 1H), 6.74 (d, 1H), 6.62 (d, 1H), 6.56 (s, 1H), 3.40 (s, 2H), 2.88–2.79 (m, 1H), 1.20 (d, 6H); MS (M+1) 485.3.

N,N-Diethyl-4-[4-(3-hydroxy-phenyl)-3,4,5,6-tetrahydro-2H-[1,2']bipyridinyl-4-yl]-benzamide. $^1$HNMR (400 MHz, CDCl$_3$) δ 8.17–8.12 (m, 1H), 7.52–7.45 (m, 1H), 6.81–6.72 (comp, 2H), 6.66 (d, 1H), 6.61–6.55 (comp, 2H), 3.70–3.42 (comp, 6H); MS (M+1) 430.4.

N,N-Diethyl-4-[4-(3-hydroxy-phenyl)-1-pyrimidin-2-yl-piperidin-4-yl]-benzamide. $^1$HNMR (400 MHz, CDCl$_3$) δ 8.27 (comp, 2H), 6.57 (s, 1H), 6.44 (d, 1H), 3.91–3.85 (comp, 2H), 3.78–3.69 (comp, 2H), 3.51–3.47 (comp, 2H); MS (M+1) 431.3.

4-[1-Benzooxazol-2-yl-4-(3-hydroxy-phenyl)-piperidin-4-yl]-N,N-diethyl-benzamide. $^1$HNMR (400 MHz, CDCl$_3$) δ 7.34 (d, 1H), 7.02 (t, 1H), 6.81–7.74 (comp, 2H), 6.62 (dd, 1H), 3.81–3.71 (comp, 2H), 3.69–3.60 (comp, 2H); MS (M+1) 470.3.

4-[4-(3-Hydroxy-phenyl)-1-(4-methyl-benzyl)-piperidin-4-yl]-N,N-dimethyl-benzamide. $^1$HNMR (400 MHz, CDCl$_3$) δ 7.07 (d, 2H), 6.75 (d, 1H), 6.61 (d, 1H), 6.45 (s, 1H), 3.34 (s, 2H), 3.05 (s, 3H), 2.92 (s, 3H), 2.27 (s, 3H); MS (M+1) 429.3.

4-[4-(3-Hydroxy-phenyl)-1-(2-methyl-pentyl)-piperidin-4-yl]-N,N-dimethyl-benzamide. $^1$HNMR (400 MHz, CDCl$_3$) δ 7.09 (t, 1H), 6.76 (d, 1H), 6.68 (s, 1H), 3.07 (s, 3H), 1.1–098 (m, 1H), 0.88–0.82 (comp, 6); MS (M+1) 409.3.

4-[4-(3-Hydroxy-phenyl)-1-(3-methyl-butyl)-piperidin-4-yl]-N,N-dimethyl-benzamide. $^1$HNMR (400 MHz, CDCl$_3$) δ 7.20–7.05 (comp, 3H), 6.77 (s, 1H), 3.06 (s, 3H), 2.94 (s, 3H), 0.84 (d, 6H); MS (M+1) 395.3.

{4-[1-(4-Fluoro-benzyl)-4-(3-hydroxy-phenyl)-piperidin-4-yl]-phenyl}-piperidin-1-yl-methanone. $^1$HNMR (400 MHz, CDCl$_3$) δ 6.96 (t, 2H), 6.78 (d, 1H), 6.61 (dd, 1H), 6.51 (s, 1H), 3.72–3.59 (comp, 2H), 3.36 (s, 2H), 3.35–3.31 (comp, 2H); MS (M+1) 473.2.

{4-[1-Hexyl-4-(3-hydroxy-phenyl)-piperidin-4-yl]-phenyl}-morpholin-4-yl-methanone. $^1$HNMR (400 MHz, CDCl$_3$) δ 7.09 (t, 1H), 6.75 (d, 1H), 6.64 (s, 1H), 6.60 (d, 1H), 3.86–3.22 (comp, 8H)0.83 (t, 3H); MS (M+1) 451.3.

EXAMPLE 5

TRIFLUORO-METHANESULFONIC ACID 3-[1-BENZYL-4-(4-DIETHYLCARBAMOYL-PHENYL)-PIPERIDIN-4-YL]-PHENYL ESTER

To a solution of 4-[1-Benzyl-4-(3-hydroxy-phenyl)-piperidin-4-yl]-N,N-diethyl-benzamide in CH$_2$Cl$_2$ (14 mL) at 0° C. was added pyridine (0.43 mL, 5.33 mmol) followed by dropwise addition of triflic anhydride (0.9 mL, 5.33 mmol) over 5 minutes. The reaction mixture was stirred at 0° C. for 1 hour and at room temperature for 2 hours. The solution was then cooled to 0° C. and 15 mL of cold saturated aqueous NaHCO$_3$ were added. The organic layer was separated and the aqueous layer was washed with CH$_2$Cl$_2$ (3×20 mL). The combined organic layers were dried (MgSO$_4$) and concentrated. The crude residue was purified by flash chromatography with hexanes/EtOAc (4:1) to afford 1.57 g (77% yield) of trifluoro-methanesulfonic acid 3-[1-benzyl-4-(4-diethylcarbamoyl-phenyl)-piperidin-4-yl]-phenyl ester. $^1$HNMR (400 MHz, CDCl$_3$) δ 7.42–7.20 (comp, 11H), 7.15–7.02 (comp, 2H), 3.63–3.43 (comp, 2H), 3.42 (s, 2H), 3.35–3.29 (comp, 2H), 2.8–2.39 (comp, 8H), 1.31–1.21 (comp, 3H), 1.21–1.08 (comp, 3H); MS (M+1) 575.2.

EXAMPLE 6

4-[1-BENZYL-4-(3-CYANO-PHENYL)-PIPERIDIN-4-YL]-N,N-DIETHYL-BENZAMIDE

To a solution of trifluoro-methanesulfonic acid 3-[1-benzyl-4-(4-diethylcarbamoyl-phenyl)-piperidin-4-yl]-phenyl ester (1.82 g, 3.16 mmol) in DMF (14 mL) was added zinc cyanide (0.26 g, 2.21 mmol) and tetrakis triphenylphosphine palladium (0.73 g, 0.63 mmol). The reaction was stirred under a nitrogen atmosphere at 90° C. for 5 hours. The mixture was cooled to room temperatures and it was diluted with diethyl ether (100 mL). The organic layer was washed with brine (5×10 mL), dried (MgSO$_4$) and concentrated. Purification with hexanes/EtOAc (1:1) afforded 1.3 g (91% yield) of 4-[1-Benzyl-4-(3-cyano-phenyl)-piperidin-4-yl]-N,N-diethyl-benzamide. $^1$HNMR (400 MHz, CDCl$_3$) δ 7.69–7.20 (comp, 13H), 3.55–3.43 (comp, 2H), 3.41 (s, 2H), 3.31–3.19 (comp, 2H), 2.6–2.25 (comp, 8H), 1.28–1.19 (comp, 3H), 1.17–1.08 (comp, 3H); MS (M+1) 452.2.

EXAMPLE 7

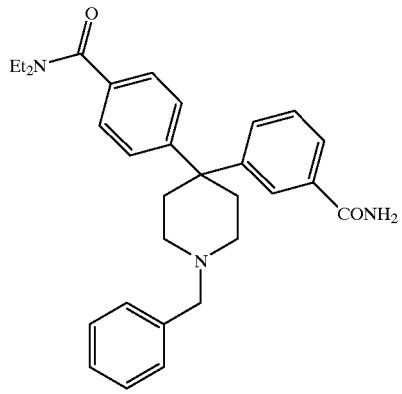

4-[1-BENZYL-4-(3-CARBOXAMIDO-PHENYL)-PIPERIDIN-4-YL]-N,N-DIETHYL-BENZAMIDE

To a solution of 4-[1-Benzyl-4-(3-cyano-phenyl)-piperidin-4-yl]-N,N-diethyl-benzamide (0.11 g, 0.24 mmol) in ethanol (0.3 mL) was added 3N aqueous Na$_2$CO$_3$ (0.6 mL) and 30% aqueous H$_2$O$_2$ (0.15 mL). The reaction mixture was stirred at room temperature for 8 hours. The mixture was diluted with water (2 mL) and the aqueous layer was washed with CH$_2$Cl$_2$ (3×5 mL). The organic layer was dried (MgSO$_4$) and concentrated. The residue was purified by flash chromatography with CH$_2$Cl$_2$/MeOH (10:1) to afford 35 mg (31% yield) of 4-[1-Benzyl-4-(3-cyano-phenyl)-piperidin-4-yl]-N,N-diethyl-benzamide. $^1$HNMR (400 MHz, CDCl3) δ 7.79 (s, 1H), 7.55–7.20 (comp, 12H), 6.13 (br, 1H), 5.62 (br, 1H), 3.48–3.40 (comp, 2H), 3.38 (s, 2H), 3,23–3.19 (comp, 2H), 2.51–2.39 (comp, 8H)1.27-1.20 (comp, 3H), 1.15–1.07 (comp, 3H); MS (M+1) 470.3.

EXAMPLE 8

1-BENZYL-4-(3-METHOXY-PHENYL)-4-(4-THIOPHEN-2-YL-PHENYL)-PIPERIDINE

To a solution of trifluoro-methanesulfonic acid 4-[1-benzyl-4-(3-methoxy-phenyl)-piperidin-4-yl]-phenyl ester (0.1 g, 0.2 mmol) in ethanol (4.5 mL) and water (0.5 mL) was added 2-thiophene boronic acid (0.052 g, 0.5 mmol) and sodium carbonate (0.037 g, 0.29 mmol) and tetrakis tripheny;phosphine palladium (0.02 g, 0.18 mmol). The reaction mixture was heated to reflux for 2 hours. The mixture was then filtered and the filtrate was concentrated under vacuum. The residue was purified by flash chromatography with hexanes/EtOAc (3:1) to afford 0.08 g (92% yield) of 1-Benzyl-4-(3-methoxy-phenyl)-4-(4-thiophen-2-yl-phenyl)-piperidine. $^1$HNMR (400 MHz, CDCl$_3$) δ 7.50 (d, 2H), 7.33–7.18 (comp, 10H), 7.07–7.00 (m, 1H), 6.89–6.63 (comp, 2H), 6.69 (d, 1H), 3.76 (s, 3H), 3.42 (s, 2H), 2.61–2.39 (comp, 8H); MS (M+1) 440.2.

The following compounds were made using a procedure analogous to that of Example 8, starting with the appropriate ester wherein R$^3$ is methoxy, hydroxy or fluoro.

3-[1-Benzyl-4-(4-thiophen-2-yl-phenyl)-piperidin-4-yl]-phenol. $^1$HNMR (400 MHz, CDCl$_3$) δ 7.46 (d, 2H), 7.16 (d, 2H), 6.80 (d, 1H), 6.59 (dd, 1H), 6.54 (s, 1H), 3.40 (s, 2H); MS (M+1) 426.0.

3-[1-Benzyl-4-(4'-trifluoromethyl-biphenyl-4-yl)-piperidin-4-yl]-phenol. $^1$HNMR (400 MHz, CDCl$_3$) δ 7.67–7.58 (comp, 4H), 7.44 (d, 2H), 7.12 (t, 1H), 6.80 (d, 1H), 6.62–6.59 (comp, 2H); MS (M+1) 488.2.

3-[1-Benzyl-4-(4'-methyl-biphenyl-4-yl)-piperidin-4-yl]-phenol. $^1$HNMR (400 MHz, CDCl$_3$) δ 7.45–7.40 (comp, 4H), 7.11 (t, 1H), 6.77 (d, 1H), 6.56 (s, 1H), 3.44 (s, 2H); MS (M+1) 434.3

3-[1-Benzyl-4-(3'-chloro-4'-fluoro-biphenyl-4-yl)-piperidin-4-yl]-phenol. $^1$HNMR (400 MHz, CDCl$_3$) δ 7.54 (dd, 1H), 7.20–7.11 (comp, 2H), 6.80 (d, 1H), 6.65 (s, 1H), 6.62 (d, 1H), 3.44 (s, 2H); MS (M+1) 472.1.

EXAMPLES 9

4-[1-BENZYL-4-(3-METHOXY-PHENYL)-PIPERIDIN-4-YL]-BENZONITRILE

To a solution of trifluoro-methanesulfonic acid 4-[1-benzyl-4-(3-methoxy-phenyl)-piperidin-4-yl]-phenyl ester (2.2 g, 4.34 mmol) in DMF (8 mL) was added zinc cyanide (0.61 g, 5.22 mmol) and tetrakis triphenylphosphine palladium (0.7 g, 0.63 mmol). The reaction was stirred under a nitrogen atmosphere at 90° C. for 5 hours. The mixture was cooled to room temperature and it was diluted with diethyl ether (100 mL). The organic layer was washed with brine (5×10 mL), dried (MgSO$_4$) and concentrated. Purification with hexanes/EtOAc (2:1) afforded 1.52 g (92% yield) of 4-[1-Benzyl-4-(3-methoxy-phenyl)-piperidin-4-yl]-benzonitrile. $^1$HNMR (400 MHz, CDCl$_3$) δ 7.51 (d, 2H), 7.34 (d, 2H), 7.28–7.18 (comp, 6H), 6.80 (d, 1H), 6.77 (s, 1H), 6.70(d, 1H), 3.75 (s, 3H), 3.39 (s, 2H), 2.63–2.39 (comp, 8H); MS (M+1) 383.2.

EXAMPLE 10

1-BENZYL-4-(3-METHOXY-PHENYL)-4-[4-(1H-TETRAZOL-5-YL)-PHENYL]-PIPERIDINE

To a solution of 4-[1-Benzyl-4-(3-methoxy-phenyl)-piperidin-4-yl]-benzonitrile (0.24 g, 0.63 mmol) in toluene (5 mL) were added dibutyltin oxide (0.025 g, 0.1 mmol) and trimethylsilyl azide (0.15 g, 1.26 mmol). The reaction mixture was heated for 60 hours. The mixture was then cooled to room temperature and concentrated under vacuum. The residue was dissolved in methanol (5 mL) and then concentrated. The residue was partitioned between saturated aqueous sodium bicarbonate solution (5 mL) and ethyl acetate. The aqueous layer was washed with ethyl acetate (3×10 mL). The combined extracts were dried (MgSO$_4$) and concentrated. Purification by flash chromatography with CH$_2$Cl$_2$/MeOH (9:1) afforded 0.19 g (71% yield) of 1-Benzyl-4-(3-methoxy-phenyl)4-[4-(1H-tetrazol-5-yl)-phenyl]-piperidine. $^1$HNMR (400 MHz, CD$_3$OD) δ 7.95 (d, 2H), 7.44–7.41 (comp, 7H), 7.23-7.18 (m, 1H), 6.90–6.77 (comp, 2H), 6.76 (d, 1H), 6.70 (d, 1H), 4.21 (s, 2H), 3.64 (s, 3H), 3.30–2.41 (comp, 8H); MS (M+1) 426.2.

EXAMPLE 11

1-BENZYL-4-[4-(4,4-DIMETHYL-4,5-DIHYDRO-OXAZOL-2-YL)-PHENYL]-4-(3-METHOXY-PHENYL)-PIPERIDINE

To a solution of 4-[1-Benzyl-4-(3-methoxy-phenyl)-piperidin-4-yl]-N-methyl-benzamide (1.01 g, 2.44 mmol), in CH₂Cl₂ (24 mL) was added pyridine (0.30 mL, 3.71 mmol). The reaction was cooled to −50° C. and triflic anhydride (0.45, 2.67 mmo) was added dropwise over 1 minutes. The reaction was stirred at −50° C. for 1.5 hours and at room temperature for 0.5 hours. The mixture was cooled to −50° C. and 2-amino-2-methyl propanol (0.36 mL, 3.77 mmol) was added. The reaction was allowed to warm to room temperature and stirred at room temperature for 16 hours. To the mixture was added water (5 mL) and the aqueous layer was extracted with CH₂Cl₂ (3×15 mL). The combined extracts were dried (MgSO₄) and concentrated. Purification by flash chromatography with hexanes/EtOAc (1:1) afforded 0.75 g (68% yield) of 1-Benzyl-4-[4-(4,4-dimethyl-4,5-dihydro-oxazol-2-yl)-phenyl]-4-(3-methoxy-phenyl)-piperidine. ¹HNMR (400 MHz, CDCl₃) δ; 7.83 (d, 2H), 7.38–7.21 (comp, 7H), 7.18 (t, 1H), 6.81–6.75 (comp, 2H), 6.63 (d, 1H), 4.08 (s, 2H), 3.78 (s, 3H), 3.41 (s, 2H), 2.79–2.40 (comp, 8H), 1.38 (s, 3H); MS (M+1) 454.2.

EXAMPLE 12

2-{4-[1-BENZYL-4-(3-METHOXY-PHENYL)-PIPERIDIN-4-YL]-PHENYL}-PROPAN-2-OL

To a solution of 4-[1-benzyl-4-(3-methoxy-phenyl)-piperidin-4-yl]-benzoic acid methyl ester (3.3 g, 7.95 mmol) in THF (30 mL) at 0° C. was added methyl magnesium bromide (3M in diethyl ether, 10.6 mL, 31.8 mmol). The ice bath was removed and the reaction was stirred at room temperature for 5 hours and at 50° C. for 5 hours. The mixture was cooled to room temperature and was quenched with slow addition of water (15 mL). The aqueous layer was washed with diethyl ether (3×30 mL). The combined extracts were dried (MgSO₄) and concentrated. Purification by flash chromatography with hexanes/EtOAc afforded 3.1 g (94%) of 2-{4-[1-Benzyl-4-(3-methoxy-phenyl)-piperidin-4-yl]-phenyl}-propan-2-ol. ¹HNMR (400 MHz, CDCl₃) δ 7.38–7-08 (comp, 10H), 6.81 (d, 1H), 6.61–6.59 (comp, 2H), 3.8 (s, 3H), 3.6 (s, 2H), 2.52–2.23 (comp, 8H), 1.42 (s, 6H); MS (M+1) 415.2.

The following compound was prepared by a procedure analogous to that of Example 12.

3-{4-[1-Benzyl-4-(3-fluoro-5-methoxy-phenyl)-piperidin-4-yl]-2-fluoro-phenyl}-pentan-3-ol. ¹HNMR (400 MHz, CDCl₃) δ 7.36 (d, 2H), 7.18 (d, 2H), 6.61 (s, 1H), 6.39 (d, 1H), 3.73 (s, 3H), 1.54 (s, 6H); MS (M+1) 434.0.

The following phenol derivatives were made using a procedure analogous to that of Example 12, followed by deprotection using the procedure of Example 4.

3-{1-(3-Cyclohexyl-propyl)-4-[4-(1-hydroxy-1-methyl-ethyl)-phenyl]-piperidin-4-yl}-phenol. ¹HNMR (400 MHz, CDCl₃) δ 6.74 (d, 1H), 6.63 (s, 1H), 6.58 (d, 1H), 2.21–2.18 (comp, 2H), 1.68–1.57 (comp, 4H), 0.82–0.79 (comp, 2H); MS (M+1) 436.3.

3-{1-Benzyl-4-[4-(1-hydroxy-1-methyl-ethyl)-phenyl]-piperidin-4-yl}-phenol. ¹HNMR (400 MHz, CDCl₃) δ 6.80 (d, 1H), 6.60–6.51 (comp, 2H), 3.39 (s, 2H), 2.55–2.18 (comp, 4H); MS (M+1) 402.2.

3-{1-Benzyl-4-[4-(1-hydroxy-1-methyl-ethyl)-phenyl]-piperidin-4-yl}-5-fluoro-phenol. ¹HNMR (400 MHz, CDCl₃) δ 7.06 (d, 2H), 6.46 (s, 1H), 6.42–6.30 (comp, 2H), 3.55 (s, 2H), 1.52 (s, 6H); MS (M+1) 420.1.

EXAMPLE 13

4-[1-BENZYL-4-(3-METHOXY-PHENYL)-PIPERIDIN-4-YL]-BENZOIC ACID HYDRAZIDE

To a solution of 4-[1-benzyl-4-(3-methoxy-phenyl)-piperidin-4-yl]-benzoic acid methyl ester (9.5 g, 22.9 mmol) in methanol (60 mL) was added hydrazine hydrate (8 mL). The reaction mixture was heated to reflux for 36 hours. The mixture was cooled to room temperature and concentrated. The residue was dissolved in toluene (50 mL) and concentrated under vacuum, and 4-[1-Benzyl-4-(3-methoxy-phenyl)-piperidin-4-yl]-benzoic acid hydrazide was obtained in quantitative yield. The residue was used in the subsequent steps without purification. ¹HNMR (400 MHz, CD₃OD) δ 7.82 (d, 1H), 7.67 (d, 1H), 7.39–7.05 (comp, 8H), 6.86 (d, 1H), 6.80 (s, 1H), 6.67 (d, 1H), 3.69 (s, 3H), 3.38 (s, 2H), 2.62–2.37 (comp, 8H); MS (M+1) 416.3.

EXAMPLE 14

CYCLOBUTANECARBOXYLIC ACID N'-{4-[1-BENZYL-4-(3-METHOXY-PHENYL)-PIPERIDIN-4-YL]-BENZOYL}-HYDRAZIDE

To a solution of 4-[1-Benzyl-4-(3-methoxy-phenyl)-piperidin-4-yl]-benzoic acid hydrazide (0.7 g, 1.69 mmol) in CH₂Cl₂ (10 mL) at 0° C. was added triethylamine (0.35 mL, 2.5 mmol) was catalytic DMAP (20 mg) and cyclobutane carbonyl chloride (0.19 mL, 1.69 mmol). The mixture was stirred at 0° C. for 1 hour and at room temperature for 5 hours. The solution was washed with brine (5 mL), dried (MgSO₄) and concentrated. Purification by flash chromatography with hexanes/EtOAc (6:4) afforded 0.63 g (75% yield) of cyclobutanecarboxylic acid N'-{4-[1-benzyl-4-(3-methoxy-phenyl)-piperidin-4-yl]-benzoyl}-hydrazide. ¹HNMR (400 MHz, CDCl₃) δ 8.59 (s, 1H), 7.67 (d, 2H), 7.41–7.08 (comp, 8H), 6.82–6.61 (comp, 3H), 3.79 (s, 3H), 2.41 (s, 2H), 3.09–3.02 (m, 1H), 2.41–2.23 (comp, 8H), 2.19–1.67 (comp, 6H); MS (M+1) 498.2.

EXAMPLE 15

1-BENZYL-4-[4-(5-CYCLOBUTYL-[1,3,4]OXADIAZOL-2-YL)-PHENYL]-4-(3-METHOXY-PHENYL)-PIPERIDINE

To a solution of cyclobutanecarboxylic acid N'-{4-[1-benzyl-4-(3-methoxy-phenyl)-piperidin-4-yl]-benzoyl}-hydrazide (0.2 g, 0.40 mmol) in CH₂Cl₂ (3 mL) was added pyridine (0.08 mL, 1.0 mmol). The reaction mixture was cooled to −78° C. Triflic anhydride (0.14 mL, 0.84 mmol) was added dropwise. The mixture was stirred at −78° C. for 1 hour and at room temperature for 2 hours. The reaction was quenched with saturated aqueous sodium bicarbonate (3 mL). The aqueous layer was washed with CH₂Cl₂ (3×5 mL) and the combined extracts were dried (MgSO₄) and concentrated. Purification by flash chromatograpy with EtOAc afforded 0.19 g (quantitative yield) of 1-Benzyl-4-[4-(5-cyclobutyl-[1,3,4]oxadiazol-2-yl)-phenyl]-4-(3-methoxy-phenyl)-piperidine. ¹HNMR (400 MHz, CDCl₃) δ 7.92 (d, 2H), 7.37 (d, 2H), 7.36–7.16 (comp, 6H), 6.83 (d, 1H), 6.80 (s, 1H), 6.60 (d, 1H), 3.81–3.78 (m, 1H), 3.77 (s, 3H), 3.45 (s, 2H), 2.82–2.38 (comp, 10H), 2.21–2.19 (comp, 2H); MS (M+1) 480.2.

The following compound was made using a procedure analogous to that of Example 15.

1-Benzyl-4-[4-(5-cyclopropyl-[1,3,4]oxadiazol-2-yl)-phenyl]-4-(3-methoxy-phenyl)-piperidine. ¹HNMR (400 MHz, CDCl₃) δ 7.92–7.81 (comp, 2H), 6.83 (d, 1H), 6.79 (s, 1H), 6.71–6.65 (m, 1H), 3.74 (s, 3H), 2.20–2.14 (m, 1H); MS (M+1) 466.4.

The following phenol derivatives were made using the procedure of Example 15, followed by deprotection using the procedure of Example 4.

3-{1-Benzyl-4-[4-(5-methyl-[1,3,4]oxadiazol-2-yl)-phenyl]-piperidin-4-yl}-phenol. ¹HNMR (400 MHz, CDCl₃) δ 7.79 (d, 2H), 7.41–7.37 (comp, 2H), 7.12 (t, 1H), 3.63 (s, 2H), 2.57 (s, 3H); MS (M+1) 426.3.

3-{1-Benzyl-4-[4-(5-cyclopropyl-[1,3,4]oxadiazol-2-yl)-phenyl]-piperidin-4-yl}-phenol. ¹HNMR (400 MHz, CDCl₃) δ 7.88–7.72 (comp, 2H), 7.56–7.42 (comp, 2H), 6.91–6.84 (m, 1H), 6.69–6.63 (m, 1H), 3.86 (s, 2H), 2.21–2.16 (m, 1H); MS (M+1) 452.2.
3-{1-Benzyl-4-[4-(5-ethyl-[1,3,4]oxadiazol-2-yl)-phenyl]-piperidin-4-yl}-phenol. ¹HNMR (400 MHz, CDCl₃) δ 7.79 (d, 2H), 7.11 (t, 1H), 7.75 (d, 1H), 6.65 (d, 1H), 6.55 (s, 1H), 2.90 (q, 2H), 1.38 (t, 3H); MS (M+1) 440.4.
3-{1-Benzyl-4-[4-(5-trifluoromethyl-[1,3,4]oxadiazol-2-yl)-phenyl]-piperidin-4-yl}-phenol. ¹HNMR (400 MHz, CDCl₃) δ 7.91 (d, 2H), 7.32 (d, 2H), 7.12 (t, 1H), 6.75 (d, 1H), 6.63–6.60 (comp, 2H), 3.42 (s, 2H); MS (M+1) 480.2.
EXAMPLE 16
Additional Synthetic Pathways
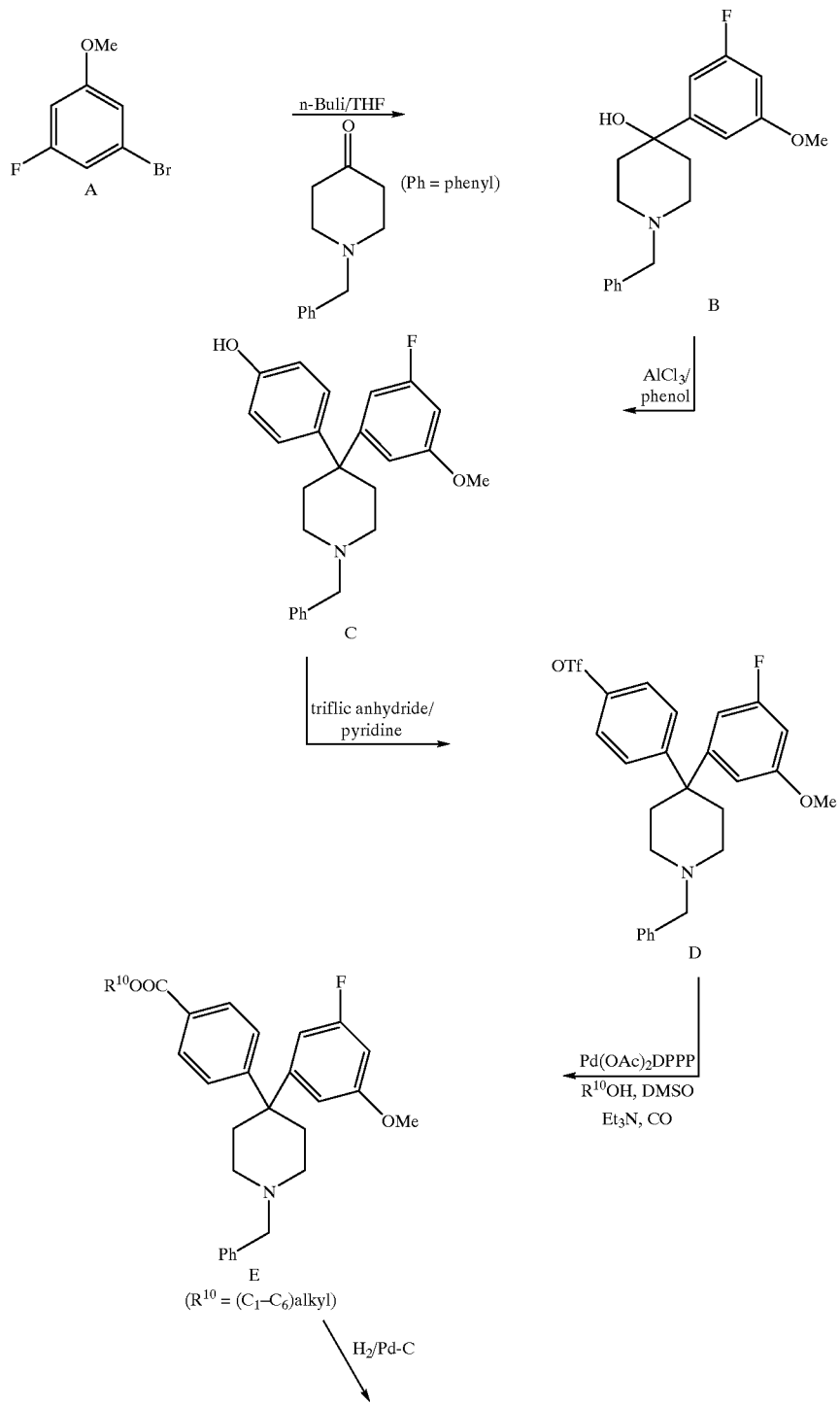

-continued
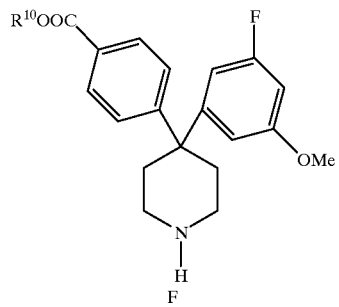
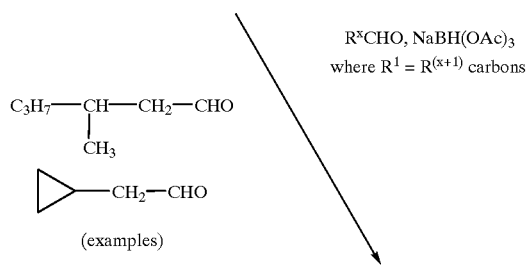
(examples)
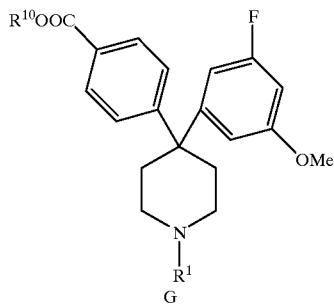
showing use of the cyclopentylmethyl group as R¹
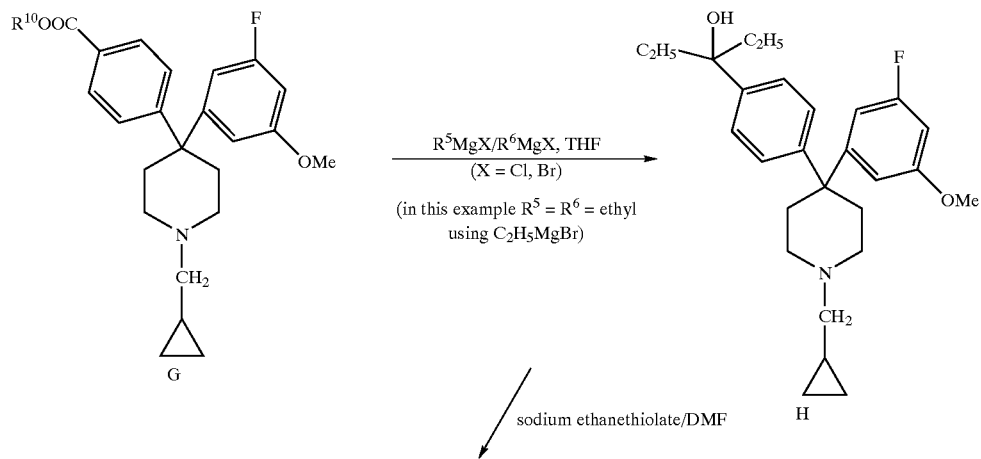

-continued
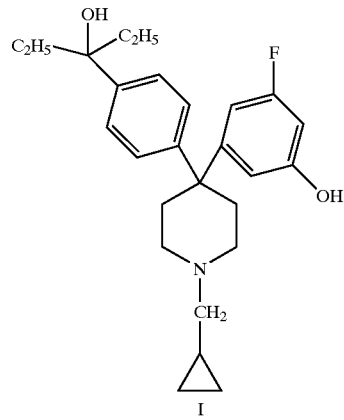
I
(completed structure where R³ is OH, but for R³ = CONH₂ continue as below)
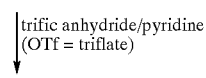
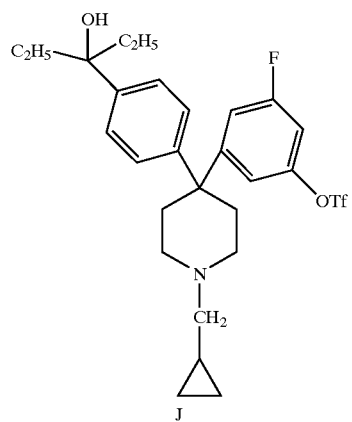
J
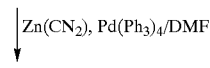
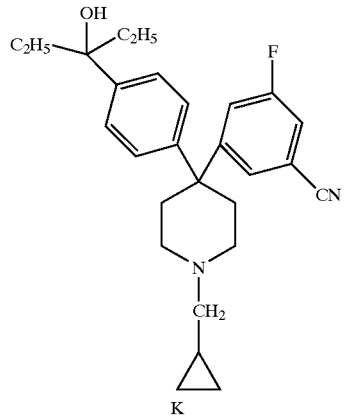
K
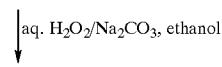

-continued

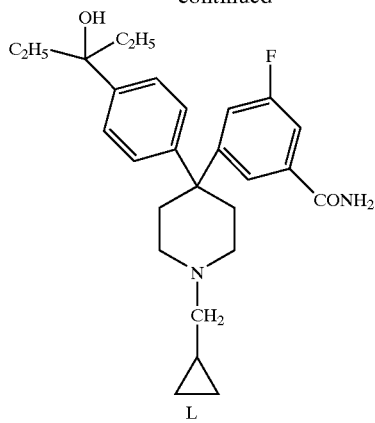

What is claimed is:
1. A compound of the formula

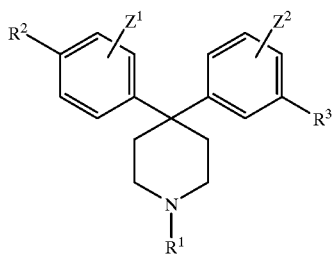

wherein $R^1$ is hydrogen, $(C_0-C_8)$alkoxy-$(C_0-C_8)$alkyl-, wherein the total number of carbon atoms is eight or fewer, aryl, aryl-$(C_1-C_8)$alkyl-, heteroaryl, heteroaryl-$(C_1-C_8)$alkyl-, heterocyclic, heterocyclic-$(C_1-C_8)$alkyl, $(C_3-C_7)$cycloalkyl-, or $(C_3-C_7)$cycloalkyl-$(C_1-C_8)$alkyl, wherein said aryl and the aryl moiety of said aryl-$(C_1-C_8)$alkyl- are selected, independently, from phenyl and naphthyl, and wherein said heteroaryl and the heteroaryl moiety of said heteroaryl-$(C_1-C_8)$alkyl- are selected, independently, from pyrazinyl, benzofuranyl, quinolyl, isoquinolyl, benzothienyl, isobenzofuryl, pyrazolyl, indolyl, isoindolyl, benzimidazolyl, purinyl, carbazolyl, 1,2,5-thiadiazolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, oxazolyl, oxadiazolyl, isoxazolyl, thiazolyl, isothiazolyl, furanyl, pyrazolyl, pyrrolyl, tetrazolyl, triazolyl, thienyl, imidazolyl, pyridinyl, benzooxazolyl and pyrimidinyl; and wherein said heterocyclic and the heterocyclic moiety of said heterocyclic-$(C_1-C_8)$alkyl- are selected from saturated or unsaturated nonaromatic monocyclic or bicyclic ring systems, wherein said monocyclic ring systems contain from four to seven ring carbon atoms, from one to three of which may optionally be replaced with O, N or S, and wherein said bicyclic ring systems contain from seven to twelve ring carbon atoms, from one to four of which may optionally be replaced with O, N or S; and wherein any of the aryl, heteroaryl or heterocyclic moieties of $R^1$ may optionally be substituted with from one to three substituents, independently selected from halo, $(C_1-C_6)$alkyl optionally substituted with from one to seven fluorine atoms, phenyl, benzyl, hydroxy, acetyl, amino, cyano, nitro, $(C_1-C_6)$alkoxy, $(C_1-C_6)$alkylamino and $[(C_1-C_6)$alkyl$]_2$amino, and wherein any alkyl moiety of the $R^1$ substituent may optionally be substituted with from one to seven fluorine atoms;

$R^2$ is aryl, heteroaryl, heterocyclic, $SO_2R^4$, $COR^4$, $CONR^5R^6$, $COOR^4$, or $C(OH)R^5R^6$ wherein each of $R^4$, $R^5$ and $R^6$ is defined, independently, as $R^1$ is defined above, or $R^5$ and $R^6$, together with the carbon or nitrogen to which they are both attached, form a three to seven membered saturated ring containing from zero to three heteroatoms selected, independently, from O, N and S, and wherein said aryl, heteroaryl, and heterocyclic are defined as such terms are defined above in the definition of $R^1$, and wherein any of the aryl, heteroaryl and heterocyclic moieties of $R^2$ may optionally be substituted with from one to three substituents, independently selected from halo, $(C_1-C_6)$alkyl optionally substituted with from one to seven fluorine atoms, phenyl, benzyl, hydroxy, acetyl, amino, cyano, nitro, $(C_1-C_6)$alkoxy optionally substituted with from one to seven fluorine atoms, $(C_1-C_6)$alkylamino and $[(C_1-C_6)$alkyl$]_2$amino;

$R^3$ is hydroxy, $(C_1-C_6)$alkoxy, $NHSO_2R^7$, $C(OH)R^7R^8$, fluorine or $CONHR^7$, wherein $R^7$ and $R^8$ are the same or different and selected from hydrogen, $(C_1-C_4)$alkyl, $(C_1-C_4)$alkoxy and $(C_1-C_4)$alkoxy-$(C_1-C_4)$alkyl having a total of 4 or less carbon atoms, and wherein any of the alkyl moieties of $R^7$ and $R^8$ may optionally be substituted with from one to seven fluorine atoms; and $Z^1$ and $Z^2$ are selected independently, from hydrogen, halo and $(C_1-C_5)$alkyl;

with the proviso that there are no two adjacent ring oxygen atoms and no ring oxygen atom adjacent to either a ring nitrogen atom or a ring sulfur atom in any of the heterocyclic or heteroaryl moieties of formula I;

or a pharmaceutically acceptable salt of such compound.

2. A compound according to claim 1 wherein $R^5$ and $R^6$ are selected, independently, from the groups set forth in the definition of $R^7$ and $R^8$.

3. A compound according to claim 1 wherein $R^1$ is cyclopropylmethyl, 3-cyclohexylpropyl, 2-phenylethyl, 2-methylpentyl, p-methylbenzyl, 2,2,2-trifluoro ethyl, or 1-methylpentyl.

4. A compound according to claim 2 wherein $R^1$ is cyclopropylmethyl, 3-cyclohexylpropyl, 2-phenylethyl, 2-methylpentyl, p-methylbenzyl, 2,2,2-trifluoroethyl, or 1-methylpentyl.

5. A compound according to claim 1 wherein $R^2$ is methyl ethyl amide, diethyl amide, a diethyl carbinol, tetrazole, or pyrazole.

6. The compound according to claim 2 wherein $R^2$ methyl ethyl amide, diethyl amide, a diethyl carbinol, tetrazole, or pyrazole.

7. A compound according to claim 1 wherein $R^3$ is hydroxy, fluoro, $CONH_2$, $NHSO_2CH_3$, or methoxy.

8. A compound according to claim 2 wherein $R^3$ is hydroxy, fluoro, $CONH_2$, $NHSO_2CH_3$, or methoxy.

9. A method of preparing a compound according to the structure

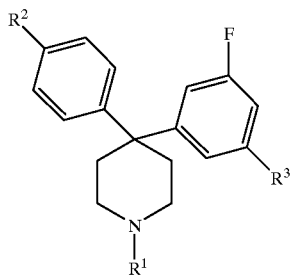

wherein $R^2$ is a dialkylcarbinol, $R^3$ is hydroxy or $CONH_2$, and $R^1$ is cyclopropylmethyl or 2-methylpentyl, comprising conducting a synthesis according to the pathway of Example 16.

10. A pharmaceutical composition comprising a therapeutically effective amount of a compound of claim 1 and a pharmaceutically acceptable carrier.

11. A method for treating a disorder or condition selected from the group consisting of arthritis, psoriasis, asthma, inflammatory bowel disease, asthma, cough and apnea, allergies, gastritis, irritable bowel syndrome, functional distension, nonulcerogeniic dyspepsia, emesis, stroke, shock, brain edema, head trauma, spinal cord trauma, cerebral ischemia, cerebral deficits subsequent to cardiac bypass surgery and grafting, urinary incontinence, addictions to or dependencies on alcohol, opiates, benzodiazepines, nicotine, heroin or cocaine, chronic pain, nonsomatic pain, acute pain, neurogenic pain, systemic lupus erythematosis, Hodgkin's disease, Sjogren's disease, epilepsy, and rejection of organ transplants or skin grafts in a mammal, comprising administering to a mammal requiring such treatment a pharmaceutical composition according to claim 10.

* * * * *